(12) United States Patent
Lee et al.

(10) Patent No.: US 8,288,386 B2
(45) Date of Patent: *Oct. 16, 2012

(54) MELANOCORTIN RECEPTOR AGONISTS

(75) Inventors: Koo Lee, Daejeon (KR); Sang Dae Lee, Daejeon (KR); Sang Pil Moon, Daejeon (KR); In Ae Ahn, Daejeon (KR); Sung Pil Choi, Daejeon (KR); Hyun Ho Lee, Daejeon (KR); Dong Sup Shim, Daejeon (KR); Soo Yong Chung, Daejeon (KR); Hyun Min Lee, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/128,725

(22) PCT Filed: Nov. 10, 2009

(86) PCT No.: PCT/KR2009/006568
§ 371 (c)(1),
(2), (4) Date: May 11, 2011

(87) PCT Pub. No.: WO2010/056022
PCT Pub. Date: May 20, 2010

(65) Prior Publication Data
US 2011/0224219 A1    Sep. 15, 2011

(30) Foreign Application Priority Data
Nov. 12, 2008 (KR) .................. 10-2008-0112403

(51) Int. Cl.
| A61K 31/496 | (2006.01) |
|---|---|
| A61K 31/501 | (2006.01) |
| A61K 31/506 | (2006.01) |
| C07D 401/14 | (2006.01) |
| C07D 403/06 | (2006.01) |
| C07D 403/14 | (2006.01) |
| C07D 405/14 | (2006.01) |
| C07D 417/14 | (2006.01) |

(52) U.S. Cl. ............ 514/252.2; 514/252.19; 514/253.09; 514/254.01; 514/254.02; 544/238; 544/295; 544/364; 544/369; 544/372

(58) Field of Classification Search .................. None
See application file for complete search history.

(56) References Cited

U.S. PATENT DOCUMENTS

| 6,534,503 B1 | 3/2003 | Dines et al. |
|---|---|---|
| 2003/0236262 A1 | 12/2003 | Bakshi et al. |
| 2004/0019094 A1 | 1/2004 | Lundstedt et al. |
| 2007/0129346 A1 | 6/2007 | Lee et al. |

FOREIGN PATENT DOCUMENTS

| JP | 2007-131570 A | 5/2007 |
|---|---|---|
| WO | WO 01/55109 A1 | 8/2001 |
| WO | WO 01/70337 A1 | 9/2001 |
| WO | WO 01/70708 A1 | 9/2001 |
| WO | WO 02/15909 A1 | 2/2002 |
| WO | WO 02/18327 A2 | 3/2002 |
| WO | WO 02/059095 A1 | 8/2002 |
| WO | WO 02/059107 A1 | 8/2002 |
| WO | WO 02/059108 A1 | 8/2002 |
| WO | WO 02/059117 A1 | 8/2002 |
| WO | WO 02/067869 A2 | 9/2002 |
| WO | WO 02/068387 A2 | 9/2002 |
| WO | WO 02/068388 A2 | 9/2002 |
| WO | WO 02/081443 A1 | 10/2002 |
| WO | WO 02/085925 A2 | 10/2002 |
| WO | WO 03/009847 A1 | 2/2003 |
| WO | WO 03/009850 A1 | 2/2003 |
| WO | WO 2004/078716 A1 | 9/2004 |
| WO | WO 2004/078717 A1 | 9/2004 |
| WO | WO 2004/087159 A1 | 10/2004 |
| WO | WO 2005/040109 A1 | 5/2005 |
| WO | WO 2005/047251 A1 | 5/2005 |
| WO | WO 2005/077935 A1 | 8/2005 |
| WO | WO 2006/019787 A2 | 2/2006 |
| WO | WO 2006/020277 A2 | 2/2006 |
| WO | WO 2006/072393 A2 | 7/2006 |
| WO | WO 2007/015157 A2 | 2/2007 |
| WO | WO 2007/015162 A1 | 2/2007 |
| WO | WO 2007/041052 A2 | 4/2007 |
| WO | WO 2007/041061 A2 | 4/2007 |
| WO | WO 2007/047496 A2 | 4/2007 |
| WO | WO 2007/096186 A1 | 8/2007 |
| WO | WO 2007/096763 A2 | 8/2007 |
| WO | WO 2007/141343 A1 | 12/2007 |
| WO | WO 2008/007930 A1 | 1/2008 |
| WO | WO 2008/039418 A2 | 4/2008 |

OTHER PUBLICATIONS

Mountjoy, Biochem. J. vol. 428,pp. 305-324 (2010).*
Tao, Endocrine Reviews,vol. 31(4),pp. 506-543 (2010).*
Bakshi, et al, "1-Amino-1,2,3,4-tetrahydronaphthalene-2-carboxylic acid as a Tic mimetic: Application in the Synthesis of Potent Human Melanocortin-4 Receptor Selective Agonists," Bioorgaic & Medicinal Chemistry Letters, vol. 15, 2005, pp. 3430-3433, Elsevier Ltd.
Greene, et al, "Protection for the Amino Group," Protective Groups in Organic Synthesis, 1991, pp. 309-405, Chapter 7, John Wiley & Sons, Inc.
Palucki et al, "Discovery of (2S)-N-[(1R)-2-[4-cyclohexyl-4[[(1,1-dimethylethyl)-amino]carbonyl]-1-piperidinyl]-1-[(4-fluorophenyl)methyl]-2-oxoethyl]-4-methyl-2-piperazinecarboxamide (MB243), a potent and selective melanocortin subtype-4 receptor agonist," Bioorganic & Medicinal Chemistry Letters, vol. 15, pp. 171-175, 2005, Elsevier Ltd.
Sebhat, et al, "Design and Pharmacology of N-[(3R)-1,2,3,4-Tetrahydroisoquinolinium-3-ylcarbonyl]-(1R)-1-(4-chlorobenzyl)-2-[4-cyclohexyl-4-(1H-1,2,4-triazol-1-ylmethyl)piperidin-1-yl]-2-oxoethylamine(1), a Potent, Selective, Melanocortin, Subtype-4 Receptor Agonist," Journal of Medicinal Chemistry, Oct. 10, 2002, pp. 4589-4593, vol. 45, No. 21, Amer. Chem. Soc.
Ye et al., "Discovery and activity of (1R,4S,6R)-N-[(1R)-2-[4-cyclohexyl-4-[[(1,1-dimethylethyl)amino]carbonyl]-1-piperidinyl]-1-[(4-fluorophenyl)methyl]-2-oxoethyl]-2-methyl-2-azabicyclo-[2.2.2]octan-6-carboxamide (3, RY764), a potent and selective melanocortin subtype-4 receptor agonist," Bioorganic & Medicinal Chem. Letters, vol. 15, 2005, pp. 3501-3505, Elsevier Ltd.
Herpin et al., "Discovery of Tyrosine-Based Potent and Selective Melanocortin-1 Receptor Small-Molecule Agonists with Anti-inflammatory Properties.", Journal of Medical Chemistry, 2003, vol, 46, pp. 1123-1126.

* cited by examiner

*Primary Examiner* — Emily Bernhardt
(74) *Attorney, Agent, or Firm* — Birch, Stewart, Kolasch & Birch, LLP

(57) ABSTRACT

The present invention relates to a compound having a good agonistic activity to melanocortin receptor, or pharmaceutically acceptable salt or isomer thereof, and an agonistic composition for melanocortin receptor comprising the same as an active ingredient.

15 Claims, No Drawings

MELANOCORTIN RECEPTOR AGONISTS

TECHNICAL FIELD

The present invention relates to a compound of the following formula 1 having a good agonistic activity to melanocortin receptor, or pharmaceutically acceptable salt or isomer thereof:

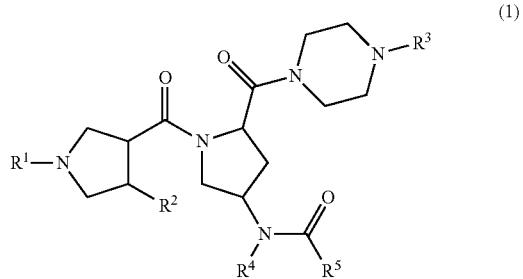

(1)

wherein R1, R2, R3, R4 and R5 are as defined below.

The present invention also relates to a process for preparing a compound of the above formula 1.

The present invention also relates to an agonistic composition for melanocortin receptor comprising a compound of the above formula 1 as an active ingredient, in particular, a composition for the prevention and treatment of obesity, diabetes, inflammation and erectile dysfunction.

BACKGROUND ART

Five subtypes of receptors have been cloned and characterized in the melanocortin family. These G-protein coupled receptors (GPCR) stimulate the cAMP signal transduction pathway in many different tissues, mediating a wide range of physiological functions. Melanocortin 1 receptor (MC1R) is mainly expressed in melanocytes, monocytes, and mast cells, to mediate pigmentation of the hair and skin and to block inflammation. MC2R is expressed in adipocytes and adrenal cells, to mediate steroidogenesis in the adrenal gland. MC3R is present in the brain, hypothalamus, heart, gut, and placenta, and has been associated with energy homeostasis and inflammation. MC4R is uniquely expressed in the brain, and controls feeding behavior, energy homeostasis, and erectile function. MC4R knock-out mice revealed the phenotype of hyperphasia and obesity. MC5R is found in a wide range of tissues and is considered to play a role for the exocrine gland system.

With a plethora of physiological functions of melanocortin receptors, a large number of compounds have been designed and synthesized in search for potent agonists and antagonists. Early examples are synthetic peptides and peptide analogues that have been identified on the basis of endogenous agonist such as MSH. These peptide agonists have been used to characterize the function of these receptors. NDP-MSH is a highly potent and nonselective agonist of MC1R, 3R, 4R and 5R, and has been reported to attenuate food intake and body weight gain in rat models. A cyclic heptapeptide MT-II is an agonist with a similar non-selective profile, and its therapeutic use has been proven in clinical trials for the treatment of erectile dysfunction.

Small molecule agonists for the melanocortin receptors have been reported to have significant activity in drug trials for the treatment of obesity, sexual dysfunction or inflammation. For example, a series of potent and selective MC4R agonists has been identified, one of which demonstrated significant effect for augmenting erectile response in mice (*J. Med. Chem.* 2002, 45, 4849). A number of MC4R agonists have also been identified, which displayed hyphophasic activity and anti-obesity effect in the rat model (*Bioorg. Med. Chem. Lett.* 2005, 15, 171, *Bioorg. Med. Chem. Lett.* 2005, 15, 3430, *Bioorg. Med. Chem. Lett.* 2005, 15, 3501). In addition, Merck & Co. Inc. has filed applications for the various compounds as MC4R agonists for patents (WO 01/55109, WO 01/70337, WO 01/70708, WO 02/081443, WO 02/15909, WO 02/067869, WO 02/068387, WO 02/068388, WO 2004/087159, WO 2004/078716, WO 2004/078717, WO 2006/019787, WO 2006/020277, WO 2007/041052, WO 2007/041061, WO 2007/047496).

Other pharmaceutical companies also have filed application for various small-molecule MCR agonists for patents (WO 02/059095, WO 02/059107, WO 02/059117, WO 02/059108, WO 02/085925, WO 03/009847, WO 03/009850, WO 02/018327, WO 2005/040109, WO 2005/047251, WO 2005/077935, WO 2005/077935, WO 2006/072393, WO 2007/015157, WO 2007/015162, JP 2007131570, WO 2007/096186, WO 2007/096763, WO 2007/141343, WO 2008/039418, WO 2008/007930).

It has also been reported that MC1R selective small molecule agonists show anti-inflammation efficacy in an acute mouse model (J Med Chem 2003, 46, 1123).

In view of the unresolved deficiencies of the various pharmaceutical compounds as discussed above, there is continuing need in the art for small molecule MCR agonists and pharmacological compositions that have improved pharmacological profiles. It is, therefore, an object of the present invention to provide novel compounds that are useful for the treatment of obesity, diabetes, erectile dysfunction and inflammation.

DISCLOSURE OF INVENTION

The aforesaid peptide MCR agonists severely have a limit for using as an orally administered drug because of their molecular characteristics. Additionally, the majority of non-peptidic small molecule MCR agonists reported up to date should be improved in aspects of oral absorbability, Blood-Brain Barrier permeability and efficacy in order for their use as a medicine.

Therefore, the object of the present invention is to provide non-peptide small molecule MCR agonists with a new structure which can be used for prevention and treatment of obesity, diabetes, erectile dysfunction and inflammation.

Specifically, the object of the present invention is to provide a non-peptide compound of formula 1 having an excellent agonistic effect on MCRs, in particular, selectively on MC4R, or pharmaceutically acceptable salt or isomer thereof.

Another object of the present invention is to provide a process for preparing the compound of formula 1.

Another object of the present invention is to provide a melanocortin receptor agonistic composition comprising the compound of the formula 1, or pharmaceutically acceptable salt or isomer thereof as an active ingredient, together with a pharmaceutically acceptable carrier.

In particular, the composition according to the present invention has a potent effect for prevention and treatment of obesity, diabetes, erectile dysfunction and inflammation.

BEST MODE FOR CARRYING OUT THE INVENTION

The present invention provides a compound of the following formula 1, or pharmaceutically acceptable salt or isomer thereof:

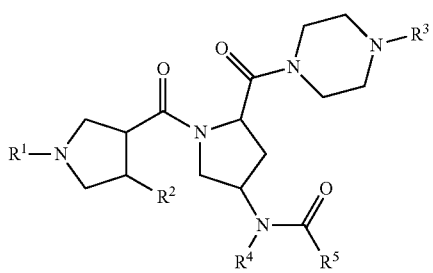

(1)

wherein

R¹ represents hydrogen, or represents $C_1$-$C_{10}$-alkyl, $C_3$-$C_7$-cycloalkyl, $C_6$-$C_{10}$-aryl, heterocycle or heteroaryl, each of which is unsubstituted or substituted with at least one substituent selected from the group consisting of halogen, amino, $C_1$-$C_4$-alkyl, trifluoromethyl, hydroxy, $C_1$-$C_4$-alkoxy, cyano and oxo;

R² represents phenyl or six-membered heteroaryl, each of which is unsubstituted or mono- or di-substituted with substituents selected from the group consisting of halogen, hydroxy, $C_1$-$C_4$-alkyl, $C_1$-$C_4$-alkoxy, cyano and amino;

R³ represents hydrogen, or represents $C_1$-$C_6$-alkyl or $C_3$-$C_7$-cycloalkyl each of which is unsubstituted or substituted with substituents selected from the group consisting of halogen, methyl, trifluoromethyl, hydroxy and amino;

R⁴ represents $C_4$-$C_7$-cycloalkyl or monocyclic heterocycle, each of which is unsubstituted or mono- or poly-substituted with substituents selected from the group consisting of halogen, hydroxy, $C_1$-$C_4$-alkyl, trifluoromethyl, $C_1$-$C_4$-alkoxy and oxo; or represents phenyl or six-membered heteroaryl, each of which is unsubstituted or mono- or di-substituted with substituents selected from the group consisting of halogen, hydroxy, $C_1$-$C_4$-alkyl, trifluoromethyl, $C_1$-$C_4$-alkoxy and amino; and R⁵ represents $C_1$-$C_6$-alkyl, difluoromethyl, trifluoromethyl, $C_3$-$C_8$-cycloalkyl, amino, $C_1$-$C_4$-alkylamino, di($C_1$-$C_4$-alkyl)amino, phenyl, monocyclic heteroaryl or monocyclic heterocycle where alkyl is unsubstituted or substituted with at least one substituent selected from the group consisting of fluoro, hydroxy, mercapto, $C_1$-$C_4$ alkoxy, acetoxy, amino, acetylamino, cyano, carbamoyl, dimethyl carbamoyl and oxo, and phenyl or heteroaryl is unsubstituted or mono- or di-substituted with substituents selected from the group consisting of halogen, hydroxy, methyl, trifluoromethyl, methoxy and amino.

In the definitions of substituents for the compound of formula (I) according to the present invention, the term "alkyl," when used alone or in combination as "alkyloxy," means straight-chain or branched-chain hydrocarbon radical. The term "cycloalkyl" represents a saturated aliphatic ring including cyclohexyl.

The term "aryl" represents 6- to 10-membered aromatic group including phenyl, naphtyl, etc.

The term "heteroaryl" represents an aromatic 3- to 6-membered ring containing 1 to 4 heteroatom(s) selected from the group consisting of nitrogen atom, oxygen atom and sulfur atom, which can be optionally fused with benzo or $C_3$-$C_8$ cycloalkyl. The examples of monocyclic heteroaryl are, but not limited to, thiazole, oxazole, thiophene, furan, pyrrole, imidazole, isoxazole, pyrazole, triazole, thiadiazole, tetrazole, oxadiazole, pyridine, pyridazine, pyrimidine, pyrazine and similar groups thereto. The examples of bicyclic heteroaryl are, but not limited to, indole, benzothiophene, benzofuran, bezimidazole, benzoxazole, benzisoxazole, benzothiazole, benzothiadiazole, benzotriazole, quinoline, isoquinoline, purine, furopyridine and similar groups thereto.

The term "heterocycle" represents a 4- to 8-membered ring containing 1 to 2 heteroatom(s) selected from the group consisting of nitrogen atom, oxygen atom, and sulfur atom, which can be optionally fused with benzo- or $C_3$-$C_8$-cycloalkyl and is saturated or unsaturated with 1 or 2 double bonds. Examples thereof are, but not limited to, piperidine, morpholine, thiamorpholine, pyrrolidine, imidazolidine, tetrahydrofuran, piperazine and similar groups thereto.

Preferred compounds among the compounds of formula 1 according to the present invention are those wherein i) R¹ represents hydrogen, methyl, ethyl, trifluoroethyl, propyl, isopropyl, butyl, isobutyl, tert-butyl, cyclopropyl, cyclobutyl, cyclopentyl or cylcohexyl; or represents phenyl, oxazolinyl, imidazolinyl, thiazolinyl, tetrahydropyranyl, tetrahydrothiopyranyl, imidazolyl, oxazolyl, thiazolyl, pyrazolyl, triazolyl, pyridinyl, pyrimidinyl, piperidinyl or piridazinyl, each of which is unsubstituted or substituted with substituent(s) selected from the group consisting of halogen, methyl, cyano, oxo and hydroxy, and more preferably, R¹ represents isopropyl, tert-butyl or cyclopropyl; or represents phenyl, tetrahydropyranyl, thiazolyl, pyridinyl, pyrimidinyl or pyridazinyl, each of which is unsubstituted or substituted with substituent(s) selected from the group consisting of halogen, methyl, cyano and hydroxy, ii) R² represents pheyl which is unsubstituted or mono- or di-substituted with substituent(s) selected from the group consisting of fluorine, chlorine, bromine, methoxy and methyl, and more preferably, R² represents 4-chloropheyl or 2,4-difluorophenyl, iii) R³ represents hydrogen, methyl, ethyl, propyl, isopropyl, butyl, isobutyl, tert-butyl, cyclopropyl, cyclobutyl or cyclopentyl, and more preferably, R³ represents hydrogen, methyl, ethyl or isopropyl, iv) R⁴ represents cyclopentyl, cyclohexyl, cycloheptyl, 4-methylcyclohexyl, 4,4-dimethylcyclohexyl, 4-fluorocyclohexyl, 4,4-difluorocyclohexyl or 4-trifluoromethylcyclohexyl; or represents phenyl which is unsubstituted or mono- or di-substituted with substituents selected from the group consisting of fluorine, chlorine, methyl and methoxy, and more preferably R⁴ represents cyclohexyl, 4-methylcyclohexyl, 4,4-dimethylcyclohexyl, 4,4-difluorocycicohexyl or 2,4-difluorophenyl, v) R⁵ represents methyl, trifluoromethyl, hydroxymethyl, methoxymethyl, ethoxymethyl, propyl, isopropyl, isobutyl, tert-butyl, —$CH_2CH_2OH$, —$CH(CH_3)CH_2OH$, —$C(CH_3)_2CH_2OH$, —$C(CH_3)(CH_2OH)_2$, —$C(CH_3)_2CH_2OMe$, —$C(CH_3)_2CH_2OEt$, phenyl, oxazolinyl, imidazolinyl, thiazolinyl, tetrahydropyranyl, imidazolyl, oxazolyl, thiazolyl, pyrazolyl, triazolyl, furanyl, tetrahydrofuranyl, dihydrofuranyl, tetrahydropyranyl, pyridinyl or piperidinyl, and more preferably, R⁵ represents isopropyl, tert-butyl, —C(CH3)2CH2OH, furanyl or tetrahydrofuranyl.

The most preferred compounds among the compounds of formula 1 according to the present invention are those wherein R¹ represents isopropyl, tert-butyl or cyclopropyl; or represents phenyl, tetrahydropyranyl, thiazolyl, pyridinyl, pyrimidinyl or pyridazinyl, each of which is unsubstituted or substituted with substituent(s) selected from the group consisting of halogen, methyl, cyano and hydroxy, R² represents 4-chloropheyl or 2,4-difluoropheyl, R³ represents hydrogen, methyl, ethyl or isopropyl, R⁴ represents cyclohexyl, 4-methylcyclohexyl, 4,4-dimethylcyclohexyl, 4,4-difluorocyclohexyl or 2,4-difluorophenyl, and R⁵ represents isopropyl, tert-butyl, —C(CH₃)₂CH₂OH, furanyl or tetrahydrofuranyl.

The representative compounds of formula 1 according to the present invention include the following listed compounds:

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)acetamide;

N-[(3S,5S)-1-{[(3S,4R)-1-tert-butyl-4-(2,4-difluorophenyl)pyrrolidin-3-yl]carbonyl}-5-(piperazin-1-ylcarbonyl)pyrrolidin-3-yl]-N-(4,4-dimethylcyclohexyl)acetamide;

(2S)—N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)-3-hydroxy-2,2-dimethylpropanamide;

N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)acetamide;

N-{(3S,5S)-1-{[(3S,4R)-1-tert-butyl-4-(2,4-difluorophenyl)pyrrolidin-3-yl]carbonyl}-5-[(4-ethylpiperazin-1-yl)carbonyl]pyrrolidin-3-yl}-N-(4,4-dimethylcyclohexyl)acetamide;

N-{(3S,5S)-1-{[(3S,4R)-1-tert-butyl-4-(2,4-difluorophenyl)pyrrolidin-3-yl]carbonyl}-5-[(4-isopropylpiperazin-1-yl)carbonyl]pyrrolidin-3-yl}-N-(4,4-dimethylcyclohexyl)acetamide;

N-{(3S,5S)-1-{[(3S,4R)-1-tert-butyl-4-(4-chlorophenyl)pyrrolidin-3-yl]carbonyl}-5-[(4-ethylpiperazin-1-yl)carbonyl]pyrrolidin-3-yl}-N-(4,4-dimethylcyclohexyl)acetamide;

N-{(3S,5S)-1-{[(3S,4R)-1-tert-butyl-4-(4-chlorophenyl)pyrrolidin-3-yl]carbonyl}-5-[(4-isopropylpiperazin-1-yl)carbonyl]pyrrolidin-3-yl}-N-(4,4-dimethylcyclohexyl)acetamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;

N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;

(2S)—N-{(3S,5S)-1-{[(3S,4R)-1-tert-butyl-4-(4-chlorophenyl)pyrrolidin-3-yl]carbonyl}-5-[(4-ethylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-1-tert-butyl-4-(4-chlorophenyl)pyrrolidin-3-yl]carbonyl}-5-[(4-isopropylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl) tetrahydrofuran-2-carboxamide;

N-{(3S,5S)-1-{[3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)-3-hydroxy-2,2-dimethylpropanamide;

(2S)—N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-2,2-dimethyl-N-(cis-4-methylcyclohexyl)propanamide;

N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-2,2-dimethyl-N-(cis-4-methylcyclohexyl)propanamide;

N-{(3S,5S)-1-{[3S,4R)-1-tert-butyl-4-(4-chlorophenyl)pyrrolidin-3-yl]carbonyl}-5-[(4-methylpiperazin-1-yl)carbonyl]pyrrolidin-3-yl}-3-hydroxy-2,2-dimethyl-N-(cis-4-methylcyclohexyl)propanamide;

N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-3-hydroxy-2,2-dimethyl-N-(cis-4-methylcyclohexyl)propanamide;

(2S)—N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-1-tert-butyl-4-(4-chlorophenyl)pyrrolidin-3-yl]-carbonyl}-5-[(4-ethylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-1-tert-butyl-4-(4-chlorophenyl)pyrrolidin-3-yl]-carbonyl}-5-[(4-isopropylpiperazin-1-yl)carbonyl]pyrrolidin-3-yl}-N-(cis-4-methylcyclohexyl)tetrahydrofuran-2-carboxamide;

N-{(3S,5S)-1-{[(3S,4R)-1-tert-butyl-4-(2,4-difluorophenyl)pyrrolidin-3-yl]-carbonyl}-5-[(4-methylpiperazin-1-yl)carbonyl]pyrrolidin-3-yl}-N-(cis-4-methylcyclohexyl)-3-furamide;

(2R)—N-{(3S,5S)-1-{[3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-difluorocyclohexyl)-2,2-dimethylpropanamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-difluorocyclohexyl)acetamide;

N-{(3S,5S)-1-{[(3S,4R)-1-tert-butyl-4-(4-chlorophenyl)pyrrolidin-3-yl]carbonyl}-5-[(4-ethylpiperazin-1-yl)carbonyl]pyrrolidin-3-yl}-N-(4,4-difluorocyclohexyl)acetamide;

N-{(3S,5S)-1-{[(3S,4R)-1-tert-butyl-4-(4-chlorophenyl)pyrrolidin-3-yl]carbonyl}-5-[(4-isopropylpiperazin-1-yl)carbonyl]pyrrolidin-3-yl}-N-(4,4-difluorocyclohexyl)acetamide;

N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-difluorocyclohexyl)-2,2-dimethylpropanamide;

(2S)—N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-difluorocyclohexyl)tetrahydrofuran-2-carboxamide;

(2S)—N-{(3S,5R)-1-{[3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

N-{(3S,5R)-1-{[3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-2,2-dimethyl-N-(cis-4-methylcyclohexyl)propanamide;

(2S)—N-{(3S,5R)-1-{[3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5R)-1-{[3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

N-{(3S,5R)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-3-hydroxy-2,2-dimethyl-N-(cis-4-m ethylcyclohexyl)propanamide;

N-{(3S,5R)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)acetamide;

N-{(3S,5R)-1-{[3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(cis-4-methylcyclohexyl)acetamide;

N-{(3S,5R)-1-{[(3S,4R)-1-tert-butyl-4-(4-chlorophenyl)pyrrolidin-3-yl]carbonyl}-5-[(4-isopropylpiperazin-1-yl)carbonyl]pyrrolidin-3-yl}-N-(c is –4-methylcyclohexyl)acetamide;

(2R)—N-{(3S,5R)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(4-chlorophenyl)-1-(6-methylpyridazine-3-yl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(2,4-difluorophenyl)-1-(6-chloropyridazine-3-yl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-4-(2,4-difluorophenyl)-1,6-dihydropyridazine-3-ylpyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(4-chlorophenyl)-1-phenylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-4-(2,4-difluorophenyl)-1-(tetrahydro-2H-pyran-4-yl)pyrrolidin-3-yl]carbonyl}-5-[(4-isopropylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(2,4-difluorophenyl)-1-(tetrahydro-2H-thiopyran-4-yl)pyrrolidin-3-yl]carbonyl}-5-[(4-isopropylpiperazin-1-yl)carbonyl]pyrrolidin-3-yl}-N-(4,4-dimethylcyclohexyl)tetrahydrofuran-2-carboxamide;

N-{(3S,5S)-1-{[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4,4-dimethylcyclohexyl)-3-hydroxy-2,2-dimethylpropanamide;

N-{(3S,5S)-1-{[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4,4-difluorocyclohexyl)-2,2-dimethylpropanamide;

(2S)—N-{(3S,5S)-1-{[[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4,4-difluorocyclohexyl)tetrahydrofuran-2-carboxamide;

(2S)—N-{(3S,5R)-1-{[(3S,4R)-4-(2,4-difluorophenyl)-1-(tetrahydro-2H-pyran-4-yl)pyrrolidin-3-yl]carbonyl}-5-[(4-isopropylpiperazin-1-yl)carbonyl]pyrrolidin-3-yl}-N-(4,4-dimethylcyclohexyl)tetrahydrofuran-2-carboxamide;

N-{(3S,5S)-1-{[3S,4R)-4-(2,4-difluorophenyl)-1-(tetrahydro-2H-pyran-4-yl)pyrrolidin-3-yl]carbonyl}-5-[(4-methylpiperazin-1-yl)carbonyl]pyrrolidin-3-yl}-2,2-dimethyl-N-(cis-4-methylcyclohexyl)propanamide;

N-{(3S,5R)-1-{[3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4-methylcyclohexyl)acetamide;

(2S)—N-{(3S,5R)-1-{[3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5R)-1-{[3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

N-{(3S,5S)-1-{[3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(4,4-dimethylcyclohexyl)-3-hydroxy-2,2-dimethylpropanamide;

N-{(3S,5S)-1-{[3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(cis-4-methylcyclohexyl)-3-hydroxy-2,2-dimethylpropanamide;

N-{(3S,5S)-1-{[[(3S,4R)-1-cyclopropyl-4-(2,4-difluorophenyl)pyrrolidin-3-yl]carbonyl}-5-[(4-methylpiperazin-1-yl)carbonyl]pyrrolidin-3-yl}-N-(cis-4-methylcyclohexyl)-3-hydroxy-2,2-dimethylpropanamide;

N-{(3S,5S)-1-{[3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(4,4-difluorocyclohexyl)-3-hydroxy-2,2-dimethylpropanamide;

N-{(3S,5R)-1-{[3S,4R)-4-(4-chlorophenyl)-1-isopropylpyrrolidin-3-yl]carbonyl}-5-[(4-methylpiperazin-1-yl)carbonyl]pyrrolidin-3-yl}-N-(cis-4-methylcyclohexyl)acetamide;

N-{(3S,5S)-1-{[3S,4R)-4-(4-chlorophenyl)-1-(6-methylpyridazine-3-yl)pyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;

N-{(3S,5S)-1-{[3S,4R)-4-(4-chlorophenyl)-1-pyridine-2-ylpyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;

(2S)—N-{(3S,5S)-1-{[3S,4R)-4-(4-chlorophenyl)-1-pyridine-2-ylpyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;
(2S)—N-{(3S,5S)-1-{[3S,4R)-4-(2,4-difluorophenyl)-1,6-dihydropyridazine-3-ylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;
N-{(3S,5S)-1-{[3S,4R)-4-(4-chlorophenyl)-1-pyrimidine-2-ylpyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;
(2S)—N-{(3S,5S)-1-{[3S,4R)-4-(2,4-difluorophenyl)-1-pyridine-2-ylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;
(2S)—N-{(3S,5S)-1-{[3S,4R)-4-(4-chlorophenyl)-1-(5-cyanopyridine-2-yl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;
N-{(3S,5S)-1-{[3S,4R)-4-(4-chlorophenyl)-1-(1,3-thiazole-2-yl)pyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;
(2S)—N-{(3S,5S)-1-{[3S,4R)-4-(4-chlorophenyl)-1-(2-methylphenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;
(2S)—N-{(3S,5S)-1-{[3S,4R)-4-(4-chlorophenyl)-1-(1-methyl-6-oxo-1,6-dihydropyridazine-3-yl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;
(2S)—N-{(3S,5S)-1-{[3S,4R)-4-(4-chlorophenyl)-1-(6-oxo-1,6-dihydropyridazine-3-yl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;
(2S)—N-{(3S,5S)-1-{[3R,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;
(2S)—N-{(3S,5S)-1-{[3S,4S)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;
(2S)—N-{(3R,5S)-1-{[3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;
(2S)—N-{(3S,5S)-1-{[3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(2,4-difluorophenyl)tetrahydrofuran-2-carboxamide;
N-[(3S,5S)-1-{[3S,4R)-1-tert-butyl-4-(4-chlorophenyl)pyrrolidin-3-yl]carbonyl}-5-(piperazin-1-ylcarbonyl)pyrrolidin-3-yl]-N-(2,4-difluorophenyl)-2-methylpropanamide;
N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(2,4-difluorophenyl)-2-methylpropanamide;
N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(2,4-difluorophenyl)-2,2-dimethylpropanamide;
N-[(3S,5S)-1-{[3S,4R)-1-tert-butyl-4-(4-chlorophenyl)pyrrolidin-3-yl]carbonyl}-5-(piperazin-1-ylcarbonyl)pyrrolidin-3-yl]-N-(2,4-difluorophenyl)-2,2-dimethylpropanamide;
N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(2,4-difluorophenyl)-2,2-dimethylpropanamide;
N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(2,4-difluorophenyl)-2-furamide; and
N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(2,4-difluorophenyl)-2-furamide.

The compounds according to the present invention also can form pharmaceutically acceptable salts. Such pharmaceutically acceptable salts include acid-addition salts formed by acid having pharmaceutically acceptable anion to form non-toxic acid addition salt including, for example, inorganic acids such as hydrochloric acid, sulfuric acid, nitric acid, phosphoric acid, hydrobromic acid, hydroiodic acid, and the like; organic carboxylic acid such as tartaric acid, formic acid, citric acid, acetic acid, trichloroacetic acid, trifluoroacetic acid, gluconic acid, benzoic acid, lactic acid, fumaric acid, maleic acid, and the like; sulfonic acid such as methanesulfonic acid, benzenesulfonic acid, p-toluenesulfonic acid or naphthalenesulfonic acid, and the like; and more preferably acid-addition salts formed by sulfuric acid, methansulfonic acid or hydrohalic acid and the like. The compounds of formula 1 according to the present invention can be converted to its salts by conventional methods.

The compounds according to the present invention can have asymmetric carbon center, and so can be present as R or S isomeric forms, racemates, diastereomeric mixtures, and individual diastereomers. The present invention encompasses all of these isomeric forms and mixtures.

In another aspect, the present invention provides a process for preparing the compound of formula 1 comprising the step of amide-coupling a compound of formula 2 with a compound of formula 3:

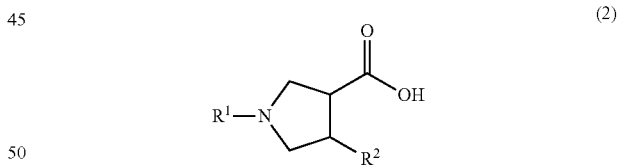

(2)

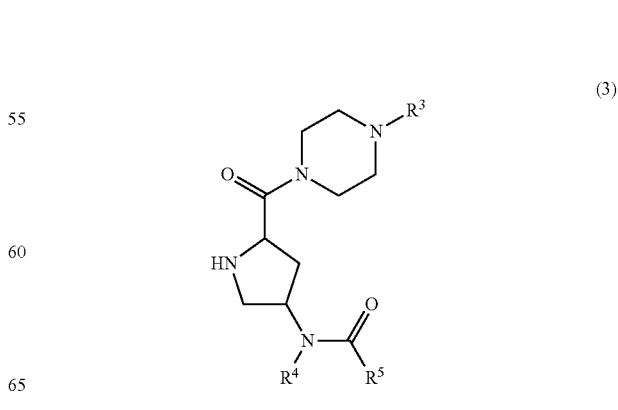

(3)

-continued

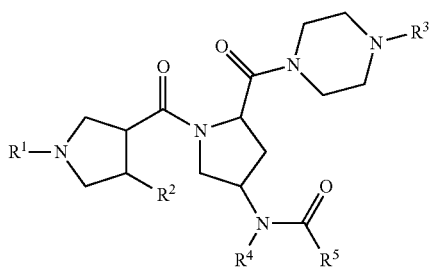
(1)

wherein $R^1$, $R^2$, $R^3$, $R^4$ and $R^5$ are the same as defined above.

Additionally, the present invention provides a process for preparing the compound of formula 1 comprising the steps of amide-coupling a compound of formula 2' with a compound of formula 3 to form a compound of formula 1'; and deprotecting the compound of formula 1':

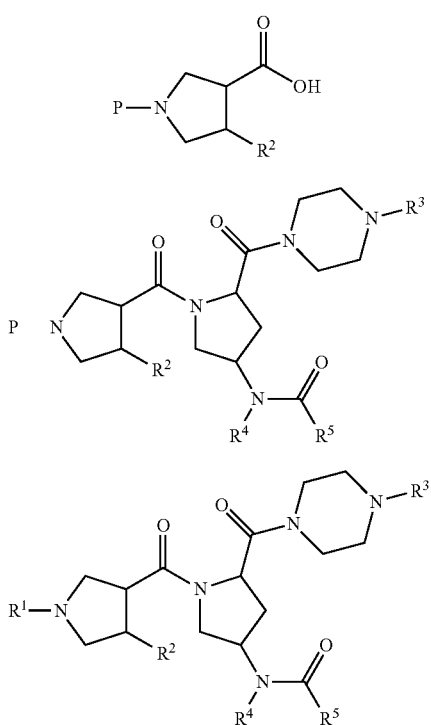

(2')

(1')

(1)

wherein
$R^1$ represents hydrogen,
$R^2$, $R^3$, $R^4$ and $R^5$ are the same as defined above, and
P represents amino-protecting group, preferably t-butoxycarbonyl(Boc), benzyloxycarbonyl(Cbz) or fluorenylmethoxycarbonyl(Fmoc).

Additionally, the present invention provides a process for preparing the compound of formula 1 comprising the steps of deprotecting the compound of formula 1' or 2' in the above process followed by i) reductive amination with $C_1$-$C_{10}$-alkyl, $C_3$-$C_7$-cycloalkyl or heterocycle including oxo-substituent or ii) coupling with arylhalide or heteroaryl halide:

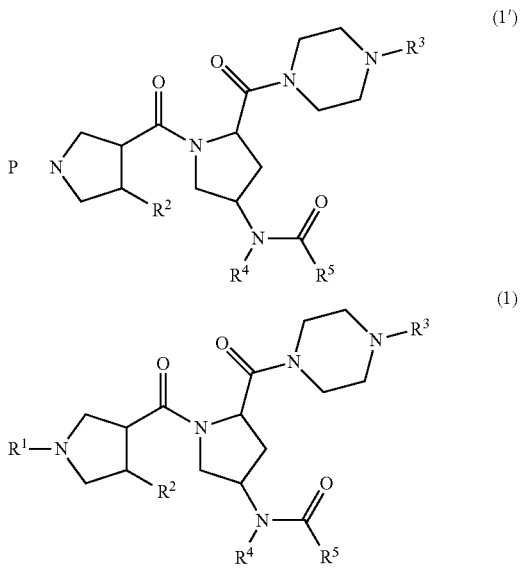

(1')

(1)

wherein
$R^1$ represents $C_1$-$C_{10}$-alkyl, $C_3$-$C_7$-cycloalkyl, $C_6$-$C_{10}$-aryl, heterocycle or heteroaryl which is unsubstituted or substituted with at least one substituent selected from the group consisting of halogen, amino, $C_1$-$C_4$-alkyl, trifluoromethyl, hydroxy, $C_1$-$C_4$-alkoxy, cyano and oxo, and
$R^2$, $R^3$, $R^4$, $R^5$ and P are the same as defined above.

It is preferable to carry out the above processes according to the present invention in a conventional solvent which has no adverse effect to the reaction, and particularly preferable to use one or more solvents selected from the group consisting of, but not limited to, dimethylformamide, dimethylacetamide, tetrahydrofuran, methylene chloride, and chloroform.

Deprotection reaction for amino groups can be carried out in the presence of strong acid such as hydrochloric acid (HCl), trifluoroacetic acid (TFA), etc., in the presence of amine base such as triethylamine, diisopropylethylamine (DIPEA) etc., or by hydrogenation. Specific reaction conditions are described in T. W. Green & G. M. Wuts, Protective Groups in Organic Synthesis, Chapter 7, pp 309-405.

Additionally, known coupling agents useful in coupling reaction are, but not limited to, carbodiimides such as dicyclohexylcarbodiimide (DCC), 1-(3-dimethylaminopropyl)-3-ethylcarbodiimide (EDC), 1,1'-dicarbonyldiimidazole (CDI), etc. in combination with 1-hydroxybenzotriazole (HOBT) or 1-hydroxy-7-azabenzotriazole (HOAT); or bis-(2-oxo-3-oxazolidinyl)-phosphinic acid chloride (BOP-Cl), diphenylphosphorylazide (DPPA), N-[dimethylamino-1H-1,2,3-triazol[4,5-b]pyridine-1-ylmethylene]-N-methylmethanaminum (HATU), etc.

The compounds of formula 1 prepared by the process of the present invention can be converted to salts thereof by conventional methods.

After the above reactions according to the process of the present invention are completed, products can be separated and purified by conventional post-treatments, for example, chromatography, recrystallization, etc.

The compounds of the present invention have potent agonistic effect against melanocortin receptors, and so the present invention provides a melanocortin receptor agonistic composition comprising the compound of formula 1, or pharmaceutically acceptable salt or isomer thereof as an active ingredient, along with pharmaceutically acceptable carrier. In particular, the composition according to the present invention has potent effect for the prevention and treatment of, but not limited to, obesity, erectile dysfunction, diabetes and inflammation.

When the compound according to the present invention is administered for clinical purpose, a preferable daily dose would be within the range of 0.01~10 mg/kg body weight as unitary dosage or separated dosage. However, a dosage level specific to individual patients can be varied, depending upon specific compound to be used, weight, sex, health condition, diet, administration time and method of drug, excretion rate, drug mixing, and severity of disease condition.

The compounds according to the present invention can be administered via any route depending on purpose. Injection, and oral and nasal administration are preferred, but the administration may be made through dermal, intraperitoneal, retroperitoneal, and rectal route.

Injection preparation, for example, aqueous or oily suspension for sterile injection, can be prepared according to known method by using proper dispersants, wetting agents or suspending agents. Solvents useful for this purpose are water, Ringer's solution, and isotonic NaCl solution. Sterilized fixed oil is also used conventionally as solvent or suspending media. Any non-irritable fixed oil including mono-, di-glyceride can be used for this purpose, and fatty acid such as oleic acid can be used for injection preparation.

Solid dosage forms for oral administration are capsules, tablets, pills, powders and granules, and in particular, capsules and tablets are useful. Tablets and pills are preferably prepared with enteric coating. Solid dosage forms can be prepared by mixing the compounds of formula 1 according to the present invention with one or more inert diluents such as sucrose, lactose, starch, etc., and carriers, for example, lubricants like magnesium stearate, disintegrants, binding agents, etc.

The present invention is described in more detail by the following Preparations and Examples, but the scope of the present invention is not limited thereby in any manner.

Abbreviations used in the following Preparations and Examples are as follows:

Ac: acetyl
AcOH: acetic acid
(Ac)$_2$O: acetic anhydride
Bn: benzyl
n-Bu: n-butyl
t-Bu: t-butyl
Bu: butyl
BOC(Boc): t-butoxycarbonyl
c-Hex: cyclohexyl
c-Bu: cyclobutyl
c-Pen: cyclopentyl
c-Pr: cyclopropyl
Cs$_2$CO$_3$: cesium carbonate
CuSO$_4$.5H$_2$O: copper (II) sulfate pentahydrate
DAST: diethylaminosulfur trifluoride
DCE: dichloroethane
DCM: dichloromethane
diMe dimethyl
diF: difluoro
DIPEA: diisopropylethylamine
DMAP: 4-dimethylaminopyridine
DMF: N,N-dimethylformamide
DMSO: dimethylsulfoxide
EDC: 1-(3-dimethylaminopropyl)-3-ethylcarbodiimide hydrochloride
Et: ethyl
EtOAc: ethyl acetate
Et2O: diethyl ether
HCl: hydrochloric acid
H$_2$O$_2$: hydrogen peroxide
Hex: normal hexane
HOBT: hydroxybenzotriazole
HBTU: 2-(1H-benzotriazole-1-yl)-1,1,3,3-tetramethyluronium hexafluorophosphate
i-Pr: isopropyl
i-Bu: isobutyl
K$_2$CO$_3$: potassium carbonate
LHMDS: lithium bis(trimethylsilyl)amide
LiBH$_4$: lithium borohydride
LiCl: lithium chloride
LiOH: lithium hydroxide
Me: methyl
MeOH methanol
MTBE: methyl t-butyl ether
MgSO$_4$: magnesium sulfate
NaBH$_4$: sodium borohydride
NaBH$_3$CN: sodium borocyanohydride
NaBH(OAc)$_3$: sodium triacetoxyborohydride
NaIO$_4$: sodium metaperiodinate
NaOtBu: sodium t-butoxide
NaOH: sodium hydroxide
NaN$_3$: sodium azide
OsO$_4$: Osmium tetroxide
Pyr: pyridine
Ph: phenyl
Pr: propyl
t-Bu: t-butyl
TEA: triethylamine
TFA: trifluoroacetic acid
THF: tetrahydrofuran Particularly, in the following Preparations and Examples, the compounds of the present invention were prepared according to the following synthesis procedures
(Reaction Schemes A & B)

[Reaction Scheme A]

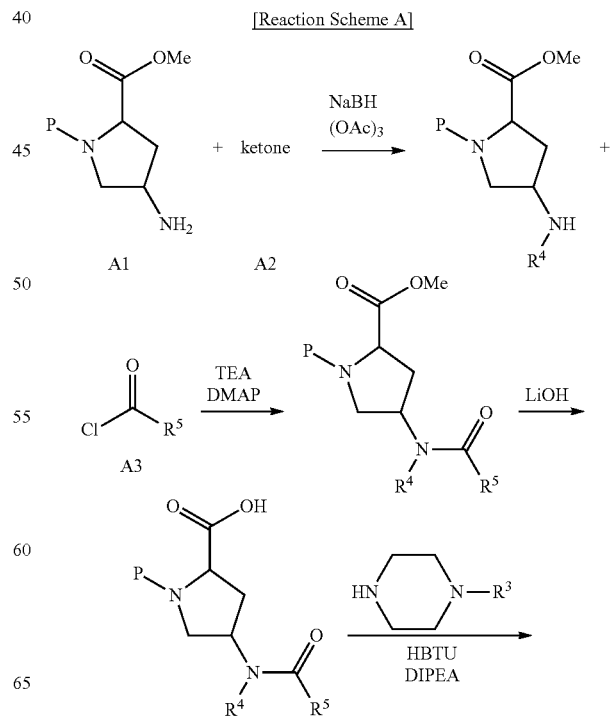

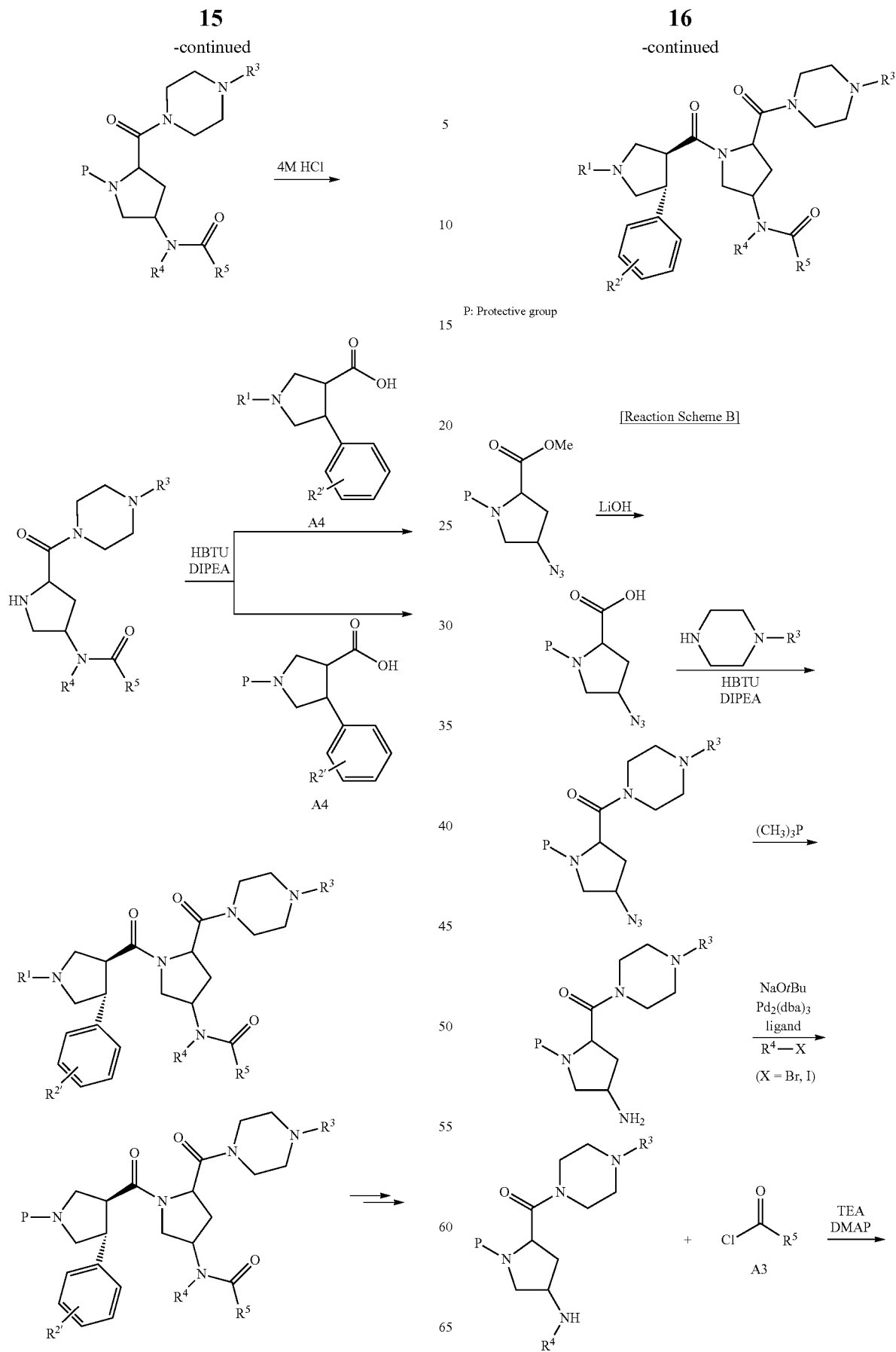

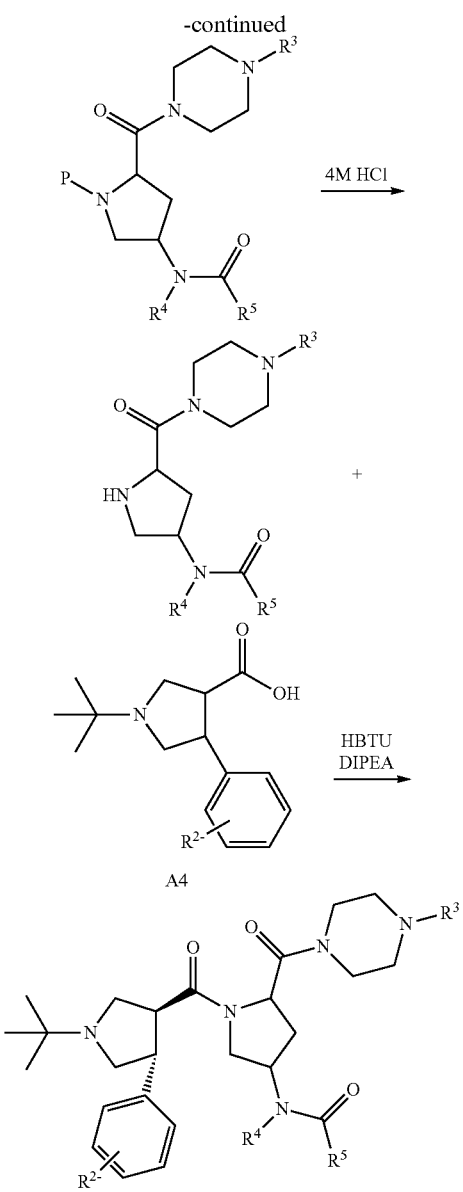

P: Protective group

The preparation methods of the Intermediate A1 compounds are follows:

Preparation 1: Methyl (2S,4S)-1-Boc-4-aminopyrrolidin-2-carboxylate

Step A: (4R)-1-Boc-4-hydroxy-L-proline (4R)-hydroxy-L-proline (5.08 g, 38.77 mmol) was dissolved in 1N NaOH (40 ml) and 1,4-dioxane (40 ml), and to the resulting solution, di-t-butyl dicarbonate (9.3 g, 42.6 mmol) was added dropwise at 0° C. The reaction mixture was stirred at room temperature for 8 hours, concentrated in vacuo, acidified with 1N HCl, and extracted with EtOAc. The organic extracts were washed with brine, dried over MgSO$_4$, filtered, and concentrated in vacuo to give the title compound (8.84 g, 99%).
MS[M+H]=232 (M+1)

Step B: Methyl (2S,4R)-1-Boc-4-hydroxypyrrolidine-2-carboxylate.

(4R)-1-Boc-4-hydroxy-L-proline (8 g, 34.63 mmol) obtained in the Step A was dissolved in DMF (80 ml) and K$_2$CO$_3$ (14 g, 101 mmol) was added thereto, and methyl iodide (2.6 ml, 51.9 mmol) was added dropwise at 0° C. The reaction mixture was stirred at room temperature for 5 hours, concentrated in vacuo, and extracted with EtOAc. The organic extracts were washed with water and brine, dried over MgSO4, filtered, and concentrated in vacuo to give the title compound (8.0 g, 95%).
MS[M+H]=246 (M+1)

Step C: Methyl (2S,4R)-1-Boc-4-[(methylsulfonyl)oxy]pyrrolidin-2-carboxylate

Methyl (2S,4R)-1-Boc-4-hydroxypyrrolidin-2-carboxylate (8 g, 32.65 mmol) obtained in the Step B was dissolved in DCM (80 ml) and TEA (11.99 ml, 81.56 mmol) was added thereto, and methanesulfonyl chloride (3.77 ml, 48.9 mmol) was added dropwise at 0° C. After the reaction mixture was stirred at room temperature for 3 hours, the organic extracts were washed with 1N HCl, saturated NaHCO$_3$ aqueous solution and brine, dried over MgSO$_4$, filtered, and concentrated in vacuo to give the title compound (9.4 g, 90%).
MS[M+H]=324 (M+1)

Step D: Methyl (2S,4S)-1-Boc-4-azidopyrrolidin-2-carboxylate

Methyl (2S,4R)-1-Boc-4-[(methylsulfonyl)oxy]pyrrolidine-2-carboxylate (9 g, 27.86 mmol) obtained in Step C was dissolved in DMF (80 ml) and NaN3 (2.7 g, 41.79 mmol) was added thereto and stirred at 90° C. for 10 hours. The reaction mixture was concentrated in vacuo, extracted with EtOAc. The organic extracts were washed with brine, dried over MgSO$_4$, filtered, and concentrated in vacuo. The residue was purified by column chromatography (eluent, EtOAc/Hex=1/4) to give the title compound (6 g, 80%).
MS[M+H]=271 (M+1)

Step E: Methyl (2S,4S)-1-Boc-4-aminopyrrolidin-2-carboxylate

Methyl (2S,4S)-1-Boc-4-azidopyrrolidin-2-carboxylate (6 g, 22.22 mmol) obtained in the Step D was dissolved in THF (15 mL) and trimethylphosphine (2.36 ml, 26.64 mmol) was added thereto dropwise at 0-5° C. The reaction mixture was stirred at room temperature for 2 hours, concentrated in vacuo, basified with a saturated NaHCO$_3$ and extracted with EtOAc twice. The organic extracts was concentrated in vacuo to give the title compound as oil (5.34 g, 98.5%).
MS[M+H]=245 (M+1)

Preparation 2: Methyl (2R,4S)-1-Boc-4-aminopyrrolidin-2-carboxylate

The title compound was prepared from (4R)-hydroxy-D-proline according to the same procedure as in Preparation 1.
MS[M+H]=245 (M+1)

Preparation 3: Methyl (2S,4R)-1-Boc-4-aminopyrrolidin-2-carboxylate

The title compound was prepared from (4S)-hydroxy-L-proline according to the same procedure as in Preparation 1.
MS[M+H]=245 (M+1)

The preparation methods of the Intermediate A2 compounds are follows:

Preparation 4: 4,4-dimethyl-cyclohexanone 4,4-dimethyl-cyclohexen-1-one (5 g, 40.3 mmol) were placed in a hydrogen reaction vessel and n-pentane (15 ml) was added, and Pd/C (500 mg) was added thereto. The hydrogen reaction vessel was pressurized with hydrogen (25 psi), and the reaction was conducted for 30 minutes. After completing the reaction, the solid like material was filtered through Celite and the filtrate was concentrated in vacuo to give the title compound (5 g, 98%).
MS[M+H]=127 (M+1)

Preparation 5: 4,4-difluoro-cyclohexanone

Step A: 8,8-difluoro-1,4-dioxospiro[4.5]decane

Commercially available 1,4-cyclohexanedion-mono-ethylene ketal (25 g, 160 mmol) was dissolved in DCM (500 ml) and DAST (52 g, 2.0 mmol) was added dropwise at 0° C. The reaction mixture was slowly warmed up to room temperature, and stirred until the reaction was completed. After confirming that all the reactants disappeared by TLC, the reaction solution was added to a saturated $NaHCO_3$ aqueous solution (700 ml) to terminate the reaction, and extracted with DCM. The organic extracts were washed with a saturated $NaHCO_3$ aqueous solution and brine, dried over $MgSO_4$, filtered, and concentrated in vacuo. The obtained residue was used in the next reaction without further purification.

Step B: 4,4-difluoro-cyclohexanone 8,8-difluoro-1,4-dioxospiro[4.5]decane obtained in the Step A was dissolved in acetone (90 ml) and 3N HCl (900 ml), and stirred until the reaction was completed. Then, the reaction mixture was extracted with DCM, washed with brine, dried over $MgSO_4$, filtered, and concentrated in vacuo. The obtained residue was used in the next reaction without further purification.
MS[M+H]=135 (M+1)

The methods for preparing commercially unavailable Intermediate A3 compounds are as follows:

Preparation 6: (2S)-tetrahydrofuran-2-carbonyl chloride (2S)-tetrahydrofuran-2-carboxylic acid (25 g, 0.215 mol) was dissolved in DCM (25 ml) and the solution was cooled to 0° C., and oxalyl chloride (43.7 g, 0.344 mol) was added dropwise thereto. DMF (500) was added to the reaction mixture and the reaction mixture was stirred at room temperature for 10 hours. Then, the reaction mixture was concentrated in vacuo at 20-30° C. until the residual volume of the reaction mixture became about 30 ml. The reaction mixture was heated at about 150-160° C. and distilled in vacuo at 80-100° C. of inner temperature to give the title compound (24 g, 82.8%).

Preparation 7: (2R)-tetrahydrofuran-2-carbonyl chloride

The title compound was prepared from (2R)-tetrahydrofuran-2-carboxylic acid according to the same procedure as in Preparation 6.

Preparation 8: Tetrahydrofuran-3-carbonyl chloride

Tetrahydrofuran-3-carboxylic acid (25 g, 0.215 mol) was dissolved in DCM (25 ml), and the solution was cooled to 0° C. and oxalyl chloride (43.7 g, 0.344 mol) was added dropwise thereto. DMF (500) was added to the reaction mixture and the reaction mixture was stirred at room temperature for 10 hours. Then, the reaction mixture was concentrated in vacuo at 20-30° C. until the residual volume of the reaction mixture became about 30 ml. The obtained residue was used in the next reaction without further purification Preparation 9: 3-furoyl chloride 3-furoic acid (25 g, 0.192 mol) was dissolved in DCM (25 ml) and the solution was cooled to 0° C. and oxalyl chloride (39.0 g, 0.307 mol) was added dropwise. DMF (500) was added to the reaction mixture and the reaction mixture was stirred at room temperature for 10 hours. Then, the reaction mixture was concentrated in vacuo at 20-30° C. until the residual volume of the reaction mixture became about 30 ml. The obtained residue was used in the next reaction without further purification Preparation 10: 2,2-dimethyl-3-acetyloxypropionyl chloride Step A: 2,2-dimethyl-3-acetyloxypropionic acid 2,2-dimethyl-3-hydroxypropionic acid (11.8 g, 100 mmol) was dissolved in pyridine (30 mL), and the reaction solution was cooled to 0° C. Acetyl chloride (11.8 g, 15.0 mmol) was slowly added dropwise, the temperature was then raised to room temperature, and the reaction solution was stirred at room temperature for 3 hours. After the reaction was completed, 1N HCl (30 mL) was added to adjust pH to 3-4, and then the reaction mixture was extracted with EtOAc. The organic extracts were washed with 1N HCl, 4-5 times, dried over $MgSO_4$, and concentrated in vacuo, give the title compound (15.2 g, 95.0%)
MS[M+H]=161 (M+1)

Step B: 2,2-dimethyl-3-acetyloxypropionyl chloride

The product of Step A, 2,2-dimethyl-3-acetyloxypropionic acid (11.76 g, 80 mmol) was dissolved in benzene (100 mL), and the reaction solution was cooled to 0° C., and then oxalyl chloride (15.0 g, 120 mmol) was slowly added dropwise. After 3 hours, the solvent was removed in vacuo, and the reaction mixture was distilled in vacuo to give the title compound.
MS[M+H]=179 (M+1)

The preparation methods of the Intermediate A4 compounds are follows:

Preparation 11: (3S,4R)-1-t-butyl-4-(2,4-difluorophenyl)pyrrolidine-3-carboxylic acid The title compound was prepared according to the procedure described in WO 2004/09126.

Preparation 12: (3S,4R)-1-t-butyl-4-(4-chlorophenyl)pyrrolidine-3-carboxylic acid The title compound was prepared from commercially obtained 2-bromo-1-(4-chlorophenyl)ethanone according to the same procedure as in Preparation 11.

Preparation 13: (3S,4R)-1-Boc-4-(2,4-difluorophenyl)pyrrolidine-3-carboxylic acid

Step A: (4R)-4-(2,4-difluorophenyl)pyrrolidine-3-carbonitrile (4R)-1-t-butyl-4-(2,4-difluorophenyl)pyrrolidine-3-carbonitrile (4 g, 15.15 mmol) which was prepared according to the procedure described in WO 2004/09126, was dissolved in DCE (10 ml) and 1-chloroethyl chloroformate (2.45 ml, 22.68 mmol) was added dropwise at 0° C. The reaction solution was heated to 70° C., and with maintaining this temperature, 1,8-bis(dimethylamino)naphthalene (4.87 g, 22.72 mmol) dissolved in DCE (10 ml) was added dropwise for 2 hours. After the reaction was completed, methanol (10 ml) was added, and with maintaining the temperature, the reaction mixture was stirred for additional 1 hour, and concentrated in vacuo. The obtained concentrate was used in the next reaction without further purification.
MS[M+1]=209 (M+1)

Step B: (4R)-1-BOC-4-(2,4-difluorophenyl)pyrrolidine-3-carbonitrile (4R)-4-(2,4-difluorophenyl)pyrrolidine-3-carbonitrile obtained in the Step A, DMAP (1.8 g, 15.15 mmol) and TEA (5.56 ml, 15.15 mmol) was dissolved in DCM (10 ml) and di-t-butyl dicarbonate (4.9 g, 22.7 mmol) was added dropwise at 0° C. The reaction mixture was stirred at room temperature for 8 hours, concentrated in vacuo, and extracted with EtOAc. The organic extracts were washed with 1N HCl and brine, dried over MgSO$_4$, concentrated in vacuo, and purified by column chromatography (eluent: EtOAc/Hex=1/6) to give the title compound (3.3 g, overall yield of Steps A and B: 72%).
MS[M+H]=309 (M+1)

Step C: (3S,4R)-1-Boc-4-(2,4-difluorophenyl)pyrrolidine-3-carboxylic acid (4R)-1-BOC-4-(2,4-difluorophenyl)pyrrolidine-3-carbonitrile (3.3 g, 10.6 mmol) obtained in Step B was dissolved in ethanol (10 ml) and 6N NaOH solution (5 ml) was added, and stirred at 70° C. for 4 hours. After the reaction was completed, the solvent was removed, the reaction mixture was diluted with ether and the organic solution was sufficiently acidified and washed with 6N HCl. The obtained organic solution was washed with brine, dried over MgSO$_4$, and concentrated in vacuo to give the title compound (3.43 g, 99.0%).
MS[M+1]=328 (M+1)

Preparation 14: (3S,4R)-1-Boc-4-(4-chlorophenyl)pyrrolidine-3-carboxylic acid The title compound was prepared from 4-chlorophenylpyrrolidine-3-carbonitrile intermediate obtained in Preparation 12 according to the same procedure as in Preparation 13.
MS[M+1]=326 (M+1)

Preparation 15: (3R,4R)-1-t-butyl-4-(4-chlorophenyl)pyrrolidin-3-carboxylic acid

Step A: (3R,4R)-1-t-butyl-4-(4-chlorophenyl)pyrrolidine-3-carbonitrile

3-{t-Butyl[(2S)-2-(4-chlorophenyl)-2-hydroxyethyl]-amino}propanenitrile (5 g, 17.80 mmol) prepared according to the process described in WO 2004/09126 was dissolved in THF (27 mL). The reaction mixture was cooled to −20° C. or less, to which was added chlorodiethylphosphate (2.69 ml, 18.70 mmol). The reaction temperature was maintained at 12~18° C., during which 1M LHMDS (37.4 ml, 37.38 mmol) was added dropwise over 2 hours. After the reaction was completed, water (45 mL) was added while the temperature was maintained at 15° C. or less. The resulting mixture was stirred for 30 minutes and extracted with EtOAc. Thus extracted organic solution was concentrated in vacuo and purified by column chromatography (eluent: EtOAc/Hex=1/3) to give the title compound (0.5 g, 10.69%).
MS[M+1]=263 (M+1)

Step B: (3R,4R)-1-t-butyl-4-(4-chlorophenyl)pyrrolidine-3-carboxylic acid

To (3R,4R)-1-t-butyl-4-(4-chlorophenyl)pyrrolidine-3-carbonitrile (0.4 g, 1.52 mmol) obtained in the Step A was added conc. HCl (10 mL), and the mixture was stirred for 5 hours at 110° C. After completing the reaction, the mixture was cooled to 20~25° C., and concentrated in vacuo. Again, the mixture was concentrated in vacuo 3 times using EtOAc. EtOAc was added to the residue, and the mixture was stirred for 3~4 hours and filtered to give the title compound (0.27 g, 62.95%).
MS[M+1]=282 (M+1)

Preparation 16: (3S,4S)-1-t-butyl-4-(4-chlorophenyl)pyrrolidin-3-carboxylic acid

Step A: (3S,4S)-1-t-butyl-4-(4-chlorophenyl)pyrrolidine-3-carbonitrile

3-{t-Butyl[2R)-2-(4-chlorophenyl)-2-hydroxyethyl]-amino}propanenitrile (5 g, 17.80 mmol) which was prepared from (R)-1-methyl-3,3-diphenyltetrahydro-pyrrole[1,2-c][1,3,2]oxazaborole over three steps according to the process described in WO 2004/09126 was reacted according to the same procedure as Step A of Preparation 15 to give the title compound (0.6 g, 12.82%).
MS[M+1]=263 (M+1)

Step B: (3S,4S)-1-t-butyl-4-(4-chlorophenyl)pyrrolidin-3-carboxylic acid

To (3S,4S)-1-t-butyl-4-(4-chlorophenyl)pyrrolidine-3-carbonitrile (0.4 g, 1.52 mmol) obtained in Step A was added conc. HCl (10 mL), and the mixture was stirred for 5 hours at 110° C. After completing the reaction, the mixture was cooled to 20~25° C., and concentrated in vacuo. Again, the mixture was concentrated in vacuo 2~3 times using DCM. DCM was added to the residue, and the mixture was stirred for 3~4 hours and filtered to give the title compound (0.19 g, 44.30%).
MS[M+1]=282 (M+1)

Preparation 17: (3S,4R)-4-(4-chlorophenyl)-1-(6-methylpyridazin-3-yl)pyrrolidine-3-carboxylic acid

Step A: Methyl (3S,4R)-4-(4-chlorophenyl)pyrrolidine-3-carboxylate (3S,4R)-1-BOC-4-(4-chlorophenyl)pyrrolidine-3-carboxylic acid (0.70 g, 2.15 mmol) obtained in Preparation 14 was dissolved in DCE (3 ml) and 4N HCl (3 ml) was added dropwise, and stirred at room temperature for 2 hours. MeOH (5 ml) was added to the reaction solution. Then, the reaction solution was stirred at room temperature for 3 hours and concentrated in vacuo. DCE (2 ml) and EtOAc (10 ml) were added to the obtained residue. Then, the reaction mixture was stirred at room temperature for 1 hour and filtered to give the title compound (0.46 g, 90.0%).

MS[M+1]=240 (M+1)

Step B: Methyl (3S,4R)-4-(4-chlorophenyl)-1-(6-methylpyridazin-3-yl)pyrrolidine-3-carboxylate The product of Step A, methyl (3S,4R)-4-(4-chlorophenyl) pyrrolidine-3-carboxylate (0.46 g, 1.92 mmol) was dissolved in dioxane (2 ml). DIPEA (1.34 ml, 7.67 mmol) and 3-chloro-6-methylpyridazine (0.74 g, 5.76 mmol) were added. The reaction was conducted at 180° C. for 5 minutes with microwave. Then, the reaction mixture was concentrated in vacuo. EtOAc was added to the obtained residue. The mixture was diluted with EtOAc, washed with water and purified by column chromatography (eluent: EtOAc/Hex=1/2) to give the title compound (0.48 g, 75%).

MS[M+H]=332 (M+1)

Step C: (3S,4R)-4-(4-chlorophenyl)-1-(6-methylpiperazin-3-yl)pyrrolidine-3-carboxylic acid The product of Step B, methyl (3S,4R)-4-(4-chlorophenyl)-1-(6-methylpyridazin-3-yl)pyrrolidine-3-carboxylate (0.48 g, 1.45 mmol) was dissolved in MeOH (4 ml) and water (0.4 ml), and LiOH (0.1 g, 4.18 mmol) was added. The reaction mixture was stirred at room temperature for 3 hours and concentrated in vacuo. The obtained residue was diluted with water. To the diluted mixture, 1N HCl (4.18 ml) was added. Then, the reaction mixture was extracted 3 times with DCE/MeOH (10/1). The organic extracts were dried over MgSO4, and concentrated under reduced to give the title compound (0.32 g, 70%).

MS[M+H]=318 (M+1)

Preparation 18: (3S,4R)-(4-chlorophenyl)-1-(1,3-thiazol-2-yl)pyrrolidine-3-carboxylic acid

Step A: Methyl (3S,4R)-4-(4-chlorophenyl)-1-(1,3-thiazol-2-yl)pyrrolidine-3-carboxylate The product of Step A in Preparation 17, methyl (3S,4R)-4-(4-chlorophenyl)pyrrolidine-3-carboxylate (0.46 g, 1.92 mmol) was dissolved in 1,4-dioxane (2 ml). DIPEA (1.34 ml, 7.67 mmol) and 2-bromo-1,3-thiazole (1.57 g, 9.6 mmol) were added. The reaction was conducted at 180° C. for 20 minutes with microwave. Then, the reaction mixture was concentrated in vacuo. The obtained residue was diluted with EtOAc, washed with water and purified by column chromatography (eluent: EtOAc/Hex=1/3) to give the title compound (0.15 g, 25%).

MS[M+H]=325 (M+1)

Step B: (3S,4R)-4-(4-chlorophenyl)-1-(1,3-thiazol-2-yl)pyrrolidine-3-carboxylic acid The title compound (0.10 g, 70%) was prepared from the product of Step A, methyl (3S,4R)-4-(4-chlorophenyl)-1-(1,3-thiazol-2-yl)pyrrolidine-3-carboxylate (0.15 g, 0.46 mmol) according to the same procedure as Step C of Preparation 17.

MS[M+H]=311 (M+1)

Preparation 19: (3S,4R)-4-(2,4-difluorophenyl)-1-(6-chloropyridazine-3-yl)pyrrolidine-3-carboxylic acid

Step A: Methyl (3S,4R)-4-(2,4-difluorophenyl)pyrrolidine-3-carboxylate

The title compound (0.46 g, 90%) was prepared from the product of Preparation 13, (3S,4R)-1-Boc-4-(2,4-difluorophenyl)pyrrolidine-3-carboxylic acid (0.70 g, 2.15 mmol) according to the same procedure as Step A of Preparation 17.

MS[M+1]=242 (M+1)

Step B: Methyl (3S,4R)-4-(2,4-difluorophenyl)-1-(6-chloropyridazin-3-yl)pyrrolidine-3-carboxylate The product of Step A, methyl (3S,4R)-4-(2,4-difluorophenyl)pyrrolidine-3-carboxylate (0.46 g, 1.91 mmol) was dissolved in dioxane (2 ml). DIPEA (1.33 mL, 7.64 mmol) and 3,6-dichloropyridazine (1.42 g, 9.55 mmol) were added. The reaction was conducted at 120° C. for 5 minutes and at 150° C. for 10 minutes with microwave. Then, the reaction mixture was concentrated in vacuo. The obtained residue was diluted with EtOAc, washed with water and purified by column chromatography (eluent: EtOAc/Hex=1/5) to give the title compound (0.44 g, 65%).

MS[M+H]=354 (M+1)

Step C: (3S,4R)-4-(2,4-difluorophenyl)-1-(6-chloropyridazin-3-yl)pyrrolidine-3-carboxylic acid The title compound (0.30 g, 70%) was prepared from the product of Step B, methyl (3S,4R)-4-(2,4-difluorophenyl)-1-(6-chloropyridazin-3-yl)pyrrolidine-3-carboxylate according to the same procedure described in Step C of Preparation 17.

MS[M+H]=340 (M+1)

Preparation 20: (3S,4R)-4-(4-chlorophenyl)-1-(6-chloropyridazin-3-yl)pyrrolidine-3-carboxylic acid The title compound (0.30 g, 70%) was prepared from the product of Preparation 14, (3S,4R)-1-Boc-4-(4-chlorophenyl)pyrrolidine-3-carboxylic acid according to the same procedure as in Preparation 19.

MS[M+1]=242 (M+1)

Preparation 21: (3S,4R)-4-(4-chlorophenyl)-1-(1,6-dihydropyridazin-3-yl)pyrrolidine-3-carboxylic acid

Step A: Methyl (3S,4R)-4-(4-chlorophenyl)-1-(1,6-dihydropyridazin-3-yl)pyrrolidine-3-carboxylate The intermediate obtained during Preparation 20, methyl (3S,4R)-4-(4-chlorophenyl)-1-(6-chloropyridazin-3-yl)pyrrolidine-3-carboxylate (1.0 g, 2.84 mmol) was dissolved in MeOH (5 mL). 1,4-cyclohexadiene (2.27 g, 28.4 mmol) and 10% Pd/C (1.0 g) were added. The reaction mixture was stirred at room temperature for 10 hours and concentrated in vacuo. The obtained residue was diluted with EtOAc and filtered through Celite. The filtrate was concentrated in vacuo and purified by column chromatography (eluent: EtOAc/Hex=1/2) to give the title compound (0.72 g, 80%).

Step B: (3S,4R)-4-(4-chlorophenyl)-1-(1,6-dihydropyridazin-3-yl)pyrrolidine-3-carboxylic acid The title compound (0.48 g, 70%) was prepared from the product of Step A, (3S,4R)-4-(4-chlorophenyl)-1-(1,6-dihydropyridazin-3-yl)pyrrolidine-3-carboxylate (0.72 g, 2.27 mmol) according to the same procedure as in Step C of Preparation 17.
MS[M+H]=304 (M+1)

Preparation 22: (3S,4R)-4-(4-chlorophenyl)-1-(6-oxo-1,6-dihydropyridazin-3-yl)pyrrolidine-3-carboxylic acid Step A: Methyl (3S,4R)-4-(4-chlorophenyl)-1-(6-oxo-1,6-dihydropyridazin-3-yl)pyrrolidine-3-carboxylate To the intermediate obtained during Preparation 20, methyl (3S,4R)-4-(4-chlorophenyl)-1-(6-chloropyridazin-3-yl)pyrrolidine-3-carboxylate (1.0 g, 2.84 mmol), AcOH(4 ml) was added. The reaction was conducted at 200° C. for 5 minutes with microwave and concentrated in vacuo. The obtained residue was diluted with EtOAc and washed with water. The organic solution was concentrated in vacuo and purified by column chromatography (eluent: EtOAc/Hex=1/1) to give the title compound (0.76 g, 80%).
MS[M+H]=334 (M+1)

Step B: (3S,4R)-4-(4-chlorophenyl)-1-(6-oxo-1,6-dihydropyridazin-3-yl)pyrrolidine-3-carboxylic acid The title compound (0.51 g, 70%) was prepared from the product of Step A, methyl (3S,4R)-4-(4-chlorophenyl)-1-(6-oxo-1,6-dihydropyridazin-3-yl)pyrrolidine-3-carboxy late (0.76 g, 2.28 mmol) according to the same procedure as in Step C of Preparation 17.
MS[M+H]=320 (M+1)

Preparation 23: (3S,4R)-4-(4-chlorophenyl)-1-(1-methyl-6-oxo-1,6-dihydropyridazin-3-yl)pyrrolidine-3-carboxylic acid Step A: Methyl (3S,4R)-4-(4-chlorophenyl)-1-(1-methyl-6-oxo-1,6-dihydropyridazin-3-yl)pyrrolidine-3-carboxylate Methyl (3S,4R)-4-(4-chlorophenyl)-1-(6-oxo-1,6-dihydropyridazin-3-yl)pyrrolidine-3-carboxylate obtained in Step A of Preparation 22 was dissolved in DMF (5 ml). $Cs_2CO_3$ (1.11 g, 3.41 mmol) was added, and methyl iodide (0.71 mL, 11.40 mmol) was added dropwise. The reaction mixture was stirred at 20-30° C. for 2 hours and concentrated in vacuo. The obtained residue was diluted with EtOAc, washed with water and purified by column chromatography (eluent: EtOAc/Hex=1/1) to give the title compound (0.55 g, 70%).
MS[M+H]=348 (M+1)

Step B: (3S,4R)-4-(4-chlorophenyl)-1-(1-methyl-6-oxo-1,6-dihydropyridazin-3-yl)pyrrolidine-3-carboxylic acid The title compound (0.37 g, 70%) was prepared from the product of Step A, methyl (3S,4R)-4-(4-chlorophenyl)-1-(1-methyl-6-oxo-1,6-dihydropyridazin-3-yl)pyrrolidine-3-carboxylate (0.55 g, 1.58 mmol) according to the same procedure as in the Step C of Preparation 17.
MS[M+H]=334 (M+1)
The compounds of the Examples synthesized by the procedure of Reaction Scheme A are as follows:

Example 1

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)acetamide TFA salt TFA salt of

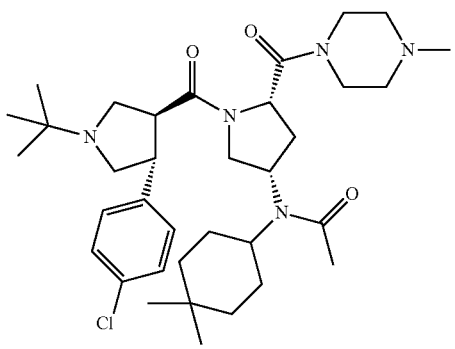

Step A: Methyl (2S,4S)-1-BOC-4-[(4,4-dimethylcyclohexyl)amino]pyrrolidine-2-carboxylate Methyl (2S,4S)-1-Boc-4-aminopyrrolidine-2-carboxylate (1.07 g, 4.38 mmol) obtained in Preparation 1 and 4,4-dimethylcyclohexanone (0.66 g, 5.25 mmol) were dissolved in DCE (10 ml), and $NaBH(OAc)_3$ (1.39 g, 6.57 mmol) was added thereto at room temperature. After the reaction mixture was stirred at room temperature for 4 hours, the organic extracts were extracted with a saturated $NaHCO_3$ aqueous solution. The extracted organic solution was dried over $MgSO_4$, filtered, and concentrated in vacuo. The obtained residue was purified by column chromatography (eluent: EtOAc/Hex=1/2) to give the title compound (1.16 g, 75%).
MS[M+H]=355 (M+1)

Step B: Methyl (2S,4S)-1-BOC-4-[acetyl(4,4-dimethylcyclohexyl)amino]pyrrolidine-2-carboxylate Methyl (2S,4S)-1-BOC-4-[(4,4-dimethylcyclohexyl)amino]pyrrolidine-2-carboxylate (1.01 g, 2.84 mmol) obtained in Step A, was dissolved in pyridine (5 mL), and Ac20 (1.34 mL, 14.20 mmol) was added thereto at room temperature. The reaction solution was heated to 90° C. and was stirred for 2 hours. After the reaction was completed, $CuSO_4.5H_2O$ aqueous solution was added and the solution was extracted with EtOAc. The extracted organic solution was dried over $MgSO_4$ and concentrated in vacuo. The obtained residue was purified by column chromatography (eluent: EtOAc/Hex=1/1) to give the title compound (0.98 g, 87%).
MS[M+H]=397 (M+1)

Step C: (4S)-1-BOC-4-[acetyl(4,4-dimethylcyclohexyl)amino]-L-proline

Methyl (2S,4S)-1-BOC-4-[acetyl(4,4-dimethylcyclohexyl)amino]pyrrolidine-2-carboxylate (0.98 g, 2.47 mmol) obtained in Step B, was dissolved in MeOH (8 mL) and water (1.6 mL). LiOH (0.18 g, 7.52 mmol) was added thereto at 0~5° C. After the reaction mixture was stirred at room temperature for 3 hours and concentrated in vacuo, the obtained residue was diluted with water and the solution was extracted with EtOAc. The extracted organic solution was washed with brine, dried over MgSO$_4$, and concentrated in vacuo to give the title compound (0.92 g, 97%).

MS[M+H]=383 (M+1)

Step D: (2S,4S)-1-BOC-4-[acetyl(4,4-dimethylcyclohexyl)amino]-2-[(4-methylpiperazin-1-yl)carbonyl]pyrrolidine (4S)-1-BOC-4-[acetyl(4,4-dimethylcyclohexyl)amino]-L-proline (0.92 g, 2.41 mmol) obtained in Step C was dissolved in DMF (10 mL) and DIPEA (1.05 mL, 6.01 mmol) was added thereto. 1-methylpiperazine (0.32 mL, 2.89 mmol) and HBTU (0.91 g, 2.41 mmol) were also added thereto in order. After the reaction solution was stirred at room temperature for 2 hours, the solution was concentrated in vacuo. The residue was diluted with EtOAc and washed with saturated NaHCO$_3$ aqueous solution. The extracted organic solution was dried over MgSO$_4$, concentrated in vacuo and purified by column chromatography (eluent:MC/MeOH=10/1) to give the title compound (1.06 g, 95%).

MS[M+H]=465 (M+1)

Step E: N-(4,4-dimethylcyclohexyl)-N-{(3S,5S)-5-[(4-methylpiperazin-1-yl)carbonyl]pyrrolidin-3-yl}acetamide (2S,4S)-1-BOC-4-[acetyl(4,4-dimethylcyclohexyl)amino]-2-[(4-methylpiperazin-1-yl)carbonyl]pyrrolidine (1.06 g, 2.28 mmol) obtained in Step D was dissolved in DCM (1 mL) and 4M HCl (1 mL) was added dropwise thereto. After the reaction solution was stirred at room temperature for 1 hour, the solution was concentrated in vacuo. The residue was concentrated in vacuo to give the title compound (830 mg, 99.8%).

MS[M+H]=365 (M+1)

Step F: N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)acetamide TFA salt N-(4,4-dimethylcyclohexyl)-N-{(3S,5S)-5-[(4-methylpiperazin-1-yl)carbonyl]pyrrolidin-3-yl}acetamide (0.83 g, 2.28 mmol) obtained in Step E was dissolved in DMF (5 mL) and DIPEA (0.99 mL, 5.69 mmol) was added thereto. (3S,4R)-1-t-butyl-4-(4-chlorophenyl)pyrrolidine-3-carboxylic acid (0.64 g, 2.28 mmol) obtain in Preparation 10 and HBTU (0.86 g, 2.28 mmol) were also added thereto in order. After the reaction solution was stirred at room temperature for 2 hours, the solution was concentrated in vacuo. The residue was diluted with EtOAc and washed with saturated NaHCO$_3$ aqueous solution. The extracted organic solution was dried over MgSO$_4$, concentrated in vacuo and purified by HPLC to give TFA salt of the title compound (1.22 g, 85%).

MS[M+H]=628 (M+1)

$^1$H NMR (500 MHz, DMSO-d6, 140° C.) δ 7.44-7.31 (m, 4H), 4.78-4.68 (br, 1H), 3.94-3.56 (m, 10H), 3.43-3.26 (m, 3H), 3.24-3.03 (m, 5H), 2.78 (s, 3H), 2.42-2.33 (m, 1H), 2.24-2.12 (br, 1H), 1.96 (s, 3H), 1.87-1.75 (m, 1H), 1.69-1.57 (br, 1H), 1.49-1.20 (m, 6H), 1.39 (s, 9H), 0.92, 0.90 (2s, 6H)

Example 2

N-[(3S,5S)-1-{[3S,4R)-1-tert-butyl-4-(2,4-difluorophenyl)pyrrolidin-3-yl]carbonyl}-5-(piperazin-1-ylcarbonyl)pyrrolidin-3-yl]-N-(4,4-dimethylcyclohexyl)acetamide TFA salt TFA salt of

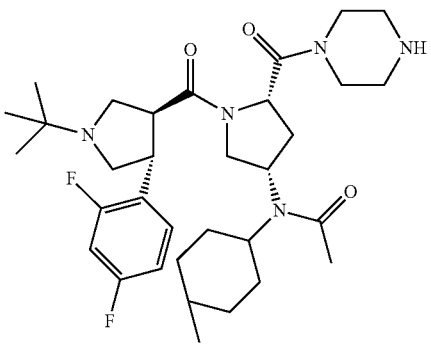

Step A: (2S,4S)-1-BOC-4-[acetyl(4,4-dimethylcyclohexyl)amino]-2-(piperazin-1-ylcarbonyl)pyrrolidine (4S)-1-BOC-4-[acetyl(4,4-dimethylcyclohexyl)amino]-L-proline (0.92 g, 2.41 mmol) obtained in Step C of Example 1, was dissolved in DMF (10 mL) and DIPEA (1.05 mL, 6.01 mmol) was added thereto. Piperazine (0.25 g, 2.89 mmol) and HBTU (0.91 g, 2.41 mmol) were also added thereto in order. After the reaction solution was stirred at room temperature for 2 hours, the solution was concentrated in vacuo. The residue was diluted with EtOAc and washed with saturated NaHCO$_3$ aqueous solution. The extracted organic solution was dried over MgSO$_4$, concentrated in vacuo. The residue was purified by column chromatography (eluent: MC/MeOH=10/1) to give the title compound (1.01 g, 93%).

MS[M+H]=451 (M+1)

Step B: N-(4,4-dimethylcyclohexyl)-N-[(3S,5S)-5-(piperazin-1-ylcarbonyl)pyrrolidin-3-yl]acetamide (2S,4S)-1-BOC-4-[acetyl(4,4-dimethylcyclohexyl)amino]-2-(piperazin-1-ylcarbonyl)pyrrolidine (1.01 g, 2.24 mmol) obtained in Step A was reacted according to the same procedure as in the Step E of Example 1 to give the title compound (784 mg, 99.8%).

MS[M+H]=351 (M+1)

Step C: N-[(3S,5S)-{[(3S,4R)-1-tert-butyl-4-(2,4-difluorophenyl)pyrrolidin-3-yl]carbonyl}-5-(piperazin-1-ylcarbonyl)pyrrolidin-3-yl]-N-(4,4-dimethylcyclohexyl)acetamide TFA salt N-(4,4-dimethylcyclohexyl)-N-[(3S,5S)-5-(piperazin-1-ylcarbonyl)pyrrolidin-3-yl]acetamide (784 mg, 2.24 mmol) obtained in Step B was dissolved in DMF (5 mL) and DIPEA (0.98 mL, 5.59 mmol) was added thereto. (3S,4R)-1-t-butyl-4-(2,4-difluorophenyl)pyrrolidine-3-carboxylic acid (0.63 g, 2.24 mmol) obtained in Preparation 11 and HBTU (0.85 g, 2.24 mmol) were added thereto in order. After the reaction solution was stirred at room temperature for 2 hours, the solution was concentrated in vacuo. The residue was diluted with EtOAc and washed with saturated NaHCO$_3$ aqueous solution. The extracted organic solution was dried over MgSO$_4$, concentrated in vacuo. The residue was purified by HPLC to give TFA salt of the title compound (1.20 g, 87%).

MS[M+H]=616 (M+1)

$^1$H NMR (500 MHz, DMSO-d$_6$, 140° C.) δ 7.64-7.50 (m, 1H), 7.11-6.96 (m, 2H), 4.77-4.64 (br, 1H), 4.04-3.48 (m, 11H), 3.46-3.17 (m, 4H), 3.17-3.01 (m, 4H), 2.45-2.33 (m, 1H), 2.26-2.12 (br, 1H), 1.97 (s, 3H), 1.88-1.72 (m, 1H), 1.68-1.50 (br, 1H), 1.49-1.20 (m, 6H), 1.38 (s, 9H), 0.91 (s, 6H)

Example 3

(2S)—N-{(3S,5S)-1-{[(3S,4R)-1-tert-butyl-4-(4-chlorophenyl)pyrrolidin-3-yl]carbon yl}-5-[(4-methylpiperazin-1-yl)carbonyl]pyrrolidin-3-yl}-N-(4,4-dimethylcyclohex yl)tetrahydrofuran-2-carboxamide TFA salt TFA salt of

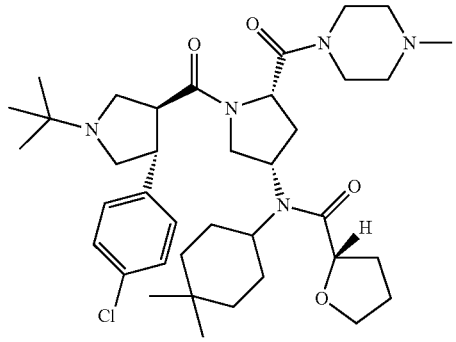

Step A: Methyl (2S,4S)-1-BOC-4-{(4,4-diemthylcyclohexyl)[(2S)-tetrahydrofuran-2-ylcarbonyl]amino}pyrrolidine-2-carboxylate Methyl (2S,4S)-1-BOC-4-[(4,4-diemthylcyclohexyl)amino]pyrrolkline-2-carboxylate obtained in Step A of Example 1 (1.01 g, 2.84 mmol) was dissolved in DCE (5 mL). TEA (5 mL) and DMAP (0.34 g, 2.84 mmol) were added thereto. (2S)-tetrahydrofuran-2-carbonyl chloride (1.14 g, 8.52 mmol) obtained in Preparation 6 was added thereto. After the reaction solution was stirred at room temperature for 2 hours and the reaction was completed, the solution was concentrated in vacuo. Saturated NaHCO$_3$ aqueous solution was added to the remaining solution and the solution was extracted with EtOAc. The extracted organic solution was washed with 1N HCl solution, dried over MgSO$_4$, concentrated in vacuo and purified by column chromatography (eluent: EtOAc/Hex=1/4) to give the title compound (1.05 g, 82%).

MS[M+H]=453 (M+1)

Step B: (4S)-1-BOC-4-{(4,4-dimethylcyclohexyl)[(2S)-tetrahydrofuran-2-ylcarbonyl]amino}-L-proline Methyl (2S,4S)-1-BOC-4-{(4,4-dimethylcyclohexyl)[(2S)-tetrahyrofuran-2-ylcarbonyl]amino}pyrrolidine-2-carboxylate (1.05 g, 2.32 mmol) obtained in Step A was reacted according to the same procedure as in the Step C of Example 1 to give the title compound (0.99 g, 97%).

MS[M+H]=439 (M+1)

Step C: (2S,4S)-1-BOC-4-{(4,4-dimethycyclohexyl)[(2S)-tetrahydrofuran-2-ylcarbonyl]amino}-2-[(4-methylpiperazin-1-yl)carbonyl]pyrrolidine (4S)-1-BOC-4-{(4,4-dimethylcyclohexyl)[2S)-tetrahydrofuran-2-ylcarbonyl]amino}-L-proline (0.99 g, 2.26 mmol) obtained in Step B was reacted according to the same procedure as in the Step D of Example 1 to give the title compound (1.12 g, 95%).

MS[M+H]=521 (M+1)

Step D: (2S)—N-(4,4-dimethylcyclohexyl)-N-{(3S,5S)-5-[(4-methylpiperazin-1-yl)carbonyl]pyrrolidin-3-yl}tetrahydrofuran-2-carboxamide (2S,4S)-1-BOC-4-{(4,4-dimethylcyclohexyl)[2S)-tetrahydrofuran-2-ylcarbonyl]amino}-2-[(4-methylpiperazin-1-yl)carbonyl]pyrrolidine (1.12 g, 2.15 mmol) obtained in Step C was reacted according to the same procedure as in the Step E of Example 1 to give the title compound (903 mg, 99.8%).

MS[M+H]=421 (M+1)

Step E: (2S)—N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide TFA salt (2S)—N-(4,4-dimethylcyclohexyl)-N-{(3S,5S)-5-[(4-methylpiperazin-1-yl)carbonyl]pyrrolidin-3-yl}tetrahydrofuran-2-carboxamide (903 mg, 2.15 mmol) obtained in Step D and (3S,4R)-1-t-butyl-4-(4-chlorophenyl)pyrrolidine-3-carboxylic acid obtained in Preparation 12 were reacted according to the same procedure as in the Step F of Example 1 to give TFA salt of the title compound (1.25 g, 85%).

MS[M+H]=684 (M+1)

$^1$H NMR (500 MHz, DMSO-d$_6$, 140° C.) δ 7.43-7.31 (m, 4H), 4.80-4.68 (br, 1H), 4.49 (dd, J=6.15, 6.1 Hz, 1H), 3.92-3.57 (m, 12H), 3.57-3.46 (m, 1H), 3.41-3.28 (m, 2H), 3.28-3.17 (m, 1H), 3.12-2.92 (m, 4H), 2.71 (s, 3H), 2.42-2.30 (m, 1H), 2.24-2.14 (br, 1H), 2.08-1.98 (m, 1H), 1.96-1.77 (m, 5H), 1.75-1.62 (m, 1H), 1.62-1.46 (m, 4H), 1.38 (s, 9H), 1.37-1.24 (m, 1H), 0.92, 0.90 (2s, 6H)

Example 4

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidine-3-yl}-N-(4,4-dimethylcyclohexyl)-3-hydroxy-2,2-dimeth ylpropanamide TFA salt TFA salt of

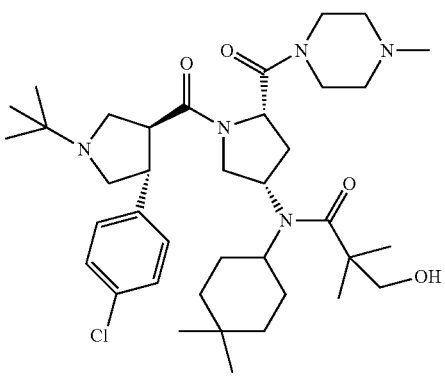

Step A: Methyl (2S,4S)-1-BOC-4-{[3-(acetoxy)-2,2-dimethylpropanoyl](4,4-dimethylcyclohexyl)amino}pyrrolidine-2-carboxylate Methyl (2S,4S)-1-BOC-4-[(4,4-dimethylcyclohexyl)amino]pyrrolidine-2-carboxylate (1.01 g, 2.84 mmol) obtained in Step A of Example 1 was dissolved in DCE (5 mL). TEA (5 mL) and DMAP (0.34 g, 2.84 mmol) were added thereto and 2,2-dimethyl-3-acetyloxypropionyl chloride (1.01 g, 5.68 mmol) obtained in Preparation 10 was added thereto. The reaction solution was heated to 90° C. and stirred for 48 hours. After the reaction was completed, the solvent was removed in vacuo. Saturated NaHCO$_3$ aqueous solution was added to the remaining solution and the solution was extracted with EtOAc. The extracted organic solution was washed with 1N HCl solution, dried over MgSO$_4$, concentrated in vacuo and purified by column chromatography (eluent: EtOAc/Hex=1/4) to give the title compound (0.88 g, 63%).

MS[M+H]=497 (M+1)

Step B: (4S)-1-BOC-4-[(4,4-dimethylcyclohexyl)(3-hydroxy-2,2-dimethylpropanoyl)amino]-L-proline Methyl (2S,4S)-1-BOC-4-{[3-(acetoxy)-2,2-dimethylpropanoyl] (4,4-dimethylcyclohexyl)amino}pyrrolidine-2-carboxylate (0.88 g, 1.77 mmol) obtained in Step A was dissolved in MeOH (8 mL) and water (1.6 mL). NaOH (213 mg, 5.31 mmol) was added thereto. The reaction solution was stirred for 12 hours. After the reaction was completed, the reaction solution was concentrated in vacuo, acidified with 1N HCl and extracted with EtOAc. The extracted organic solution was washed with 1N HCl solution, dried over MgSO$_4$ and concentrated in vacuo to give the title compound (0.74 g, 95%).

MS[M+H]=441 (M+1)

Step C: (2S,4S)-1-BOC-4-[(4,4-dimethylcyclohexyl)(3-hydroxy-2,2-dimethylpropanoyl)amino]-2-[(4-methylpiperazin-1-yl)carbonyl]pyrrolidine (4S)-1-BOC-4-[(4,4-dimethylcyclohexyl)(3-hydroxy-2,2-dimethylpropanoyl)amino]-L-proline (0.74 g, 1.68 mmol) obtained in Step B was reacted according to the same procedure as in the Step D of Example 1 to give the title compound (0.83 g, 95%).

MS[M+H]=523 (M+1)

Step D: N-(4,4-diemthylcyclohexyl)-3-hydroxy-2,2-dimethyl-N-{(3S,5S)-5-[(4-methylpiperazin-1-yl)carbonyl]pyrrolidin-3-yl}propanamide (2S,4S)-1-BOC-4-[(4,4-dimethylcyclohexyl)(3-hydroxy-2,2-dimethylpropanoyl)amino]-2-[(4-methylpiperazin-1-yl)carbonyl]pyrrolidine (0.83 g, 1.59 mmol) obtained in Step C was reacted according to the same procedure as in the Step E of Example 1 to give the title compound (0.67, 99.8%).

MS[M+H]=423 (M+1)

Step E: N-{(3S,5S)-1-{[(3S,4R)-1-tert-butyl-4-(4-chlorophenyl)pyrrolidin-3-yl]carbonyl}-5-[(4-methylpiperazin-1-yl) carbonyl]pyrrolidin-3-yl}-N-(4,4-dimethylcyclohexyl)-3-hydroxy-2,2-dimethylpropan amide TFA salt N-(4,4-dimethylcyclohexyl)-3-hydroxy-2,2-dimethyl-N-{(3S,5S)-5-[(4-methylpiperazin-1-yl)carbonyl]pyrrolidin-3-yl}propanamide (0.67 g, 1.59 mmol) obtained in Step D and (3S,4R)-1-t-butyl-4-(4-chlorophenyl)pyrrolidine-3-carboxylic acid obtained in Preparation 12 were reacted according to the same procedure as in the Step F of Example 1 to give TFA salt of the title compound (0.92 g, 85%).

MS[M+H]=686 (M+1)

$^1$H NMR (500 MHz, DMSO-d$_6$, 140° C.) δ 7.43-7.31 (m, 4H), 4.78-4.68 (br, 1H), 3.94-3.55 (m, 10H), 3.44-3.26 (m, 3H), 3.24-2.91 (m, 7H), 2.78 (s, 3H), 2.42-2.32 (m, 1H), 2.23-2.11 (br, 1H), 1.85-1.73 (m, 1H), 1.68-1.56 (br, 1H), 1.47-1.18 (m, 6H), 1.39 (s, 9H), 1.14 (s, 6H), 0.92, 0.90 (2s, 6H)

Examples 5~15

Compounds of Preparations 1-23 were reacted according to the same procedure as Examples 1~4 to give compounds of following Examples.

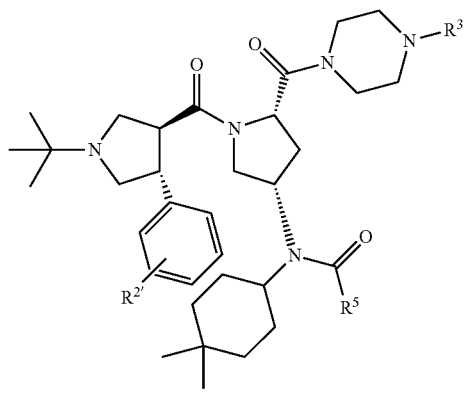

| Example | R2' | R3 | R5 | MS (M+1) |
|---|---|---|---|---|
| 5 | 2,4-diF | Me | Me | 630 |
| 6 | 2,4-diF | Et | Me | 644 |
| 7 | 2,4-diF | i-Pr | Me | 658 |
| 8 | 4-Cl | Et | Me | 642 |
| 9 | 4-Cl | i-Pr | Me | 656 |
| 10 | 4-Cl | Me | t-Bu | 670 |
| 11 | 2,4-diF | Me | t-Bu | 672 |
| 12 | 4-Cl | Et | (tetrahydrofuran-2-yl) | 698 |
| 13 | 4-Cl | i-Pr | (tetrahydrofuran-2-yl) | 712 |
| 14 | 2,4-diF | Me | (tetrahydrofuran-2-yl) | 686 |
| 15 | 2,4-diF | Me | C(CH$_3$)$_2$CH$_2$OH | 688 |

Example 5

TFA Salt $^1$H NMR (500 MHz, DMSO-d$_6$, 140° C.) δ 7.66-7.53 (m, 1H), 7.12-6.97 (m, 2H), 4.76-4.64 (br, 1H), 4.04-3.80 (m, 3H), 3.80-3.56 (m, 7H), 3.45-3.27 (m, 3H), 3.27-3.17 (m, 1H), 3.17-3.02 (m, 4H), 2.77 (s, 3H), 2.46-2.35 (m, 1H), 2.23-2.12 (br, 1H), 1.97 (s, 3H), 1.85-1.73 (m, 1H), 1.64-1.50 (br, 1H), 1.47-1.20 (m, 6H), 1.38 (s, 9H), 0.91 (s, 6H)

Example 7

TFA Salt $^1$H NMR (500 MHz, DMSO-d$_6$, 140° C.) δ 7.65-7.54 (m, 1H), 7.10-6.97 (m, 2H), 4.77-4.66 (br, 1H), 4.03-3.80 (m, 3H), 3.80-3.60 (m, 7H), 3.47-3.27 (m, 4H), 3.27-3.19 (m, 1H), 3.19-3.02 (m, 4H), 2.47-2.35 (m, 1H), 2.23-2.12 (br, 1H), 1.97 (s, 3H), 1.86-1.73 (m, 1H), 1.67-1.55 (br, 1H), 1.47-1.20 (m, 6H), 1.38 (s, 9H), 1.27, 1.25 (2s, 6H), 0.91 (s, 6H)

Example 8

TFA Salt $^1$H NMR (500 MHz, DMSO-d$_6$, 140° C.) δ 7.43-7.33 (m, 4H), 4.78-4.68 (br, 1H), 3.93-3.56 (m, 10H), 3.43-3.26 (m, 3H), 3.23-3.03 (m, 7H), 2.43-2.33 (m, 1H), 2.22-2.11 (br, 1H), 1.96 (s, 3H), 1.87-1.76 (m, 1H), 1.69-1.57 (br, 1H), 1.48-1.20 (m, 6H), 1.39 (s, 9H), 1.24 (t, 3H), 0.92, 0.90 (2s, 6H)

Example 11

TFA Salt $^1$H NMR (500 MHz, DMSO-d$_6$, 140° C.) δ 7.66-7.56 (m, 1H), 7.10-6.98 (m, 2H), 4.77-4.67 (br, 1H), 4.07-3.91 (m, 2H), 3.89-3.57 (m, 8H), 3.57-3.46 (m, 1H), 3.44-3.28 (m, 2H), 3.20-3.04 (m, 5H), 2.78 (s, 3H), 2.52-2.40 (m, 1H), 2.17-2.06 (br, 1H), 1.92-1.79 (m, 1H), 1.66-1.54 (br, 1H), 1.49-1.18 (m, 6H), 1.39 (s, 9H), 1.16 (s, 9H), 0.92 (s, 6H)

Example 16

(2S)—N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide HCl salt HCl salt of

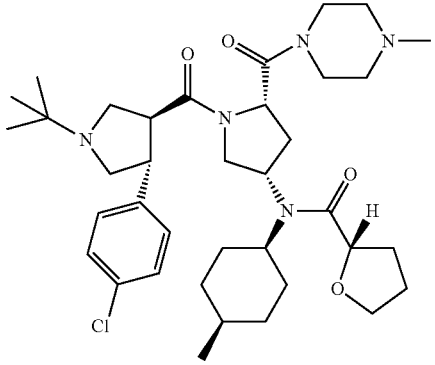

Step A: Methyl (2S,4S)-1-BOC-4-[(cis-4-methylcyclohexyl)amino]pyrrolidine-2-carboxylate Methyl (2S,4S)-1-Boc-4-aminopyrrolidine-2-carboxylate (1.07 g, 4.38 mmol) obtained in Preparation 1 and 4-methylcyclohexanone were dissolved in DCE (30 mL) and NaBH(OAc)$_3$ (1.39 g, 6.57 mmol) was added thereto at room temperature. After the reaction solution was stirred for 4 hours at room temperature, saturated NaHCO$_3$ aqueous solution was added thereto and the solution was extracted with DCM (50 mL×2) and EtOAc. The extracted organic solution was washed with brine, dried over MgSO$_4$, filtered and concentrated in vacuo. Cis- and trans-compounds were separated from the obtained residue by column chromatography (eluent: EtOAc/Hex=1/2) to give the title compound (0.84 g, 57%).

MS[M+H]=341 (M+1)

Step B: Methyl (2S,4S)-1-BOC-4-{(cis-4-methylcyclohexyl)[(2S)-tetrahydrofuran-2-ylcarbonyl]amino}pyrrolidine-2-carboxylate Methyl (2S,4S)-1-BOC-4-[(cis-4-methylcyclohexyl)amino]pyrroldine-2-carboxylate (0.84 g, 2.49 mmol) obtained in Step A was reacted according to the same procedure as in the Step A of Example 3 to give the title compound (0.92 g, 87%).
MS[M+H]=439 (M+1)

Step C: (4S)-1-BOC-4-{(cis-4-methylcyclohexyl)[(2S)-tetrahydrofuran-2-ylcarbonyl]amino}-L-proline Methyl (2S,4S)-1-BOC-4-{(cis-4-methylcyclohexyl)[(2S)-tetrahydrofuran-2-ylcarbonyl]amino}pyrrolidine-2-carboxylate (0.92 g, 2.10 mmol) obtained in Step B was reacted according to the same procedure as in the Step C of Example 1 to give the title compound (0.85 g, 95%).
MS[M+H]=425 (M+1)

Step D: (2S,4S)-1-BOC-4-{(cis-4-methylcyclohexyl)[(2S)-tetrahydrofuran-2-ylcarbonyl]amino}-2-[(4-methylpiperazin-1-yl)carbonyl]pyrrolidine (4S)-1-BOC-4-{(cis-4-methylcyclohexyl)[2S)-tetrahydrofuran-2-ylcarbonyl]amino}-L-proline (0.85 g, 2.00 mmol) obtained in Step C was reacted according to the same procedure as in the Step D of Example 1 to give the title compound (0.95 g, 94%).
MS[M+H]=507 (M+1)

Step E: (2S)—N-(cis-4-methylcyclohexyl)-N-{(3S,5S)-5-[(4-methylpiperazin-1-yl)carbonyl]pyrrolidin-3-yl}tetrahydrofuran-2-carboxamide (2S,4S)-1-BOC-4-{(cis-4-methylcyclohexyl)[2S)-tetrahydrofuran-2-ylcarbonyl]amino}-2-[(4-methylpiperazin-1-yl)carbonyl]pyrrolidine (0.95 g, 1.87 mmol) obtained in Step D was reacted according to the same procedure as in the Step E of Example 1 to give the title compound (0.76 g, 99.8%).
MS[M+H]=407 (M+1)

Step F: (2S)—N-{(3S,5S)-1-{[(3S,4R)-1-tert-butyl-4-(4-chlorophenyl)pyrrolidin-3-yl]carbonyl}-5-[(4-methylpiperazin-1-yl) carbonyl]pyrrolidin-3-yl}-N-(cis-4-methylcyclohexyl)tetrahydrofuran-2-carboxamide TFA salt (2S)—N-(cis-4-methylcyclohexyl)-N-{(3S,5S)-5-[(4-methylpiperazin-1-yl)carbonyl]pyrrolidin-3-yl}tetrahydrofuran-2-carboxamide (0.76 g, 1.87 mmol) obtained in Step E and (3S,4R)-1-t-butyl-4-(4-chlorophenyl)pyrrolidine-3-carboxylic acid obtained in Preparation 12 were reacted according to the same procedure as in the Step F of Example 1 to give the title compound (1.10 g, 88%).
MS[M+H]=670 (M+1)

Step G: (2S)—N-{(3S,5S)-1-{[(3S,4R)-1-tert-butyl-4-(4-chlorophenyl)pyrrolidin-3-yl]carbonyl}-5-[(4-methylpiperazin-1-yl) carbonyl]pyrrolidin-3-yl}-N-(cis-4-methylcyclohexyl)tetrahydrofuran-2-carboxamide HCl salt TFA salt of the compound obtained in Step F was basified with 1N NaOH and extracted with EtOAc. This organic solution was dried over MgSO$_4$, concentrated in vacuo and 4M HCl/dioxane was added thereto. The reaction solution was stirred for 1 hour at room temperature and concentrated in vacuo without further purification to give HCl salt.

$^1$H NMR (500 MHz, DMSO-d$_6$, 140° C.) δ 7.54-7.22 (m, 4H), 4.79-4.65 (br, 1H), 4.53-4.43 (m, 1H), 3.96-3.58 (m, 10H), 3.58-3.37 (m, 2H), 3.37-3.22 (m, 2H), 3.22-2.94 (m, 5H), 2.73 (s, 3H), 2.64-2.50 (m, 1H), 2.43-2.27 (m, 1H), 2.20-2.09 (m, 1H), 2.09-1.97 (m, 1H), 1.97-1.74 (m, 5H), 1.61-1.44 (m, 4H), 1.40 (s, 9H), 1.37-1.22 (m, 3H), 0.95 (s, 3H)

Examples 17~25

Compounds of Preparations 1-23 were reacted according to the same procedure as Examples 1~4, 16 to give compounds of following Examples.

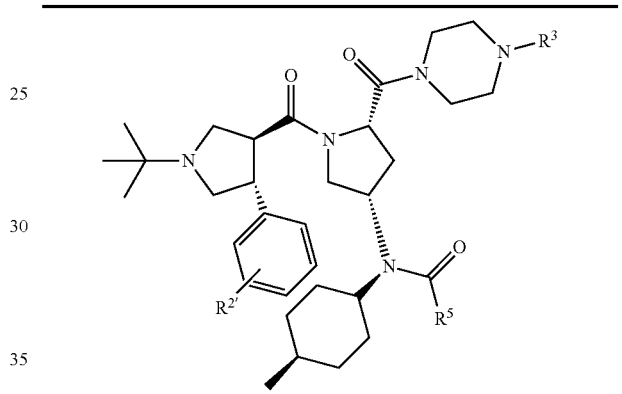

| Example | R$^{2'}$ | R$^3$ | R$^5$ | MS (M + 1) |
|---|---|---|---|---|
| 17 | 4-Cl | Me | t-Bu | 656 |
| 18 | 2,4-diF | Me | t-Bu | 658 |
| 19 | 4-Cl | Me | C(CH$_3$)$_2$CH$_2$OH | 672 |
| 20 | 2,4-diF | Me | C(CH$_3$)$_2$CH$_2$OH | 674 |
| 21 | 2,4-diF | Me |  | 672 |
| 22 | 4-Cl | Et | 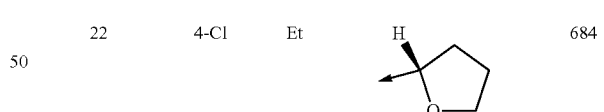 | 684 |
| 23 | 4-Cl | i-Pr | 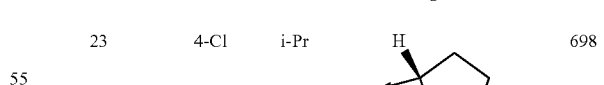 | 698 |
| 24 | 2,4-diF | Me |  | 668 |
| 25 | 4-Cl | Me |  | 670 |

Example 17

TFA Salt

¹H NMR (500 MHz, DMSO-d$_6$, 140° C.) δ 7.44-7.29 (m, 4H), 4.79-4.67 (br, 1H), 3.99-3.88 (m, 1H), 3.86-3.47 (m, 10H), 3.43-3.28 (m, 2H), 3.18-2.99 (m, 5H), 2.75 (s, 3H), 2.48-2.40 (m, 1H), 2.16-2.05 (m, 1H), 1.94-1.81 (m, 2H), 1.66-1.48 (m, 5H), 1.43-1.18 (m, 2H), 1.39 (s, 9H), 1.15 (s, 9H), 0.98 (d, 3H)

Example 26

N-{(3S,5S)-1-{[(3S,4R)-1-tert-butyl-4-(4-chlorophenyl)pyrrolidine-3-yl]carbonyl}-5-[(4-methylpiperazin-1-yl)carbonyl]pyrrolidin-3-yl}-N-(4,4-difluorocyclohexyl)-2,2-dimethylpropanamide TFA salt TFA salt of

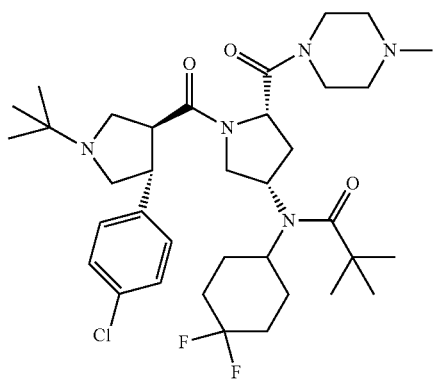

Step A: Methyl (2S,4S)-1-BOC-4-[(4,4-difluorocyclohexyl)amino]pyrrolidine-2-carboxylate Methyl (2S,4S)-1-Boc-4-aminopyrrolidine-2-carboxylate (29 g, 120 mmol) obtained in Preparation 1 and 4,4-difluorocyclohexanone (19.31 g, 144 mmol) obtained in Preparation 5 was dissolved in DCE. NaBH(OAc)$_3$ (37 g, 180 mmol) was added thereto. The reaction solution was stirred for 6 hours at room temperature. After the reaction was completed, the solution was concentrated in vacuo and NaHCO$_3$ aqueous solution was added thereto. The solution was extracted with EtOAc, dried over MgSO$_4$, concentrated in vacuo and purified by column chromatography (eluent: EtOAc/Hex=1/4) to give the title compound (23.66 g, 55%) separated from methyl (2S,4S)-1-BOC-4-[(4'-fluorocyclohex-3-en-1-yl)amino]pyrrolidine-2-carboxylate.
MS[M+H]=363 (M+1)

Step B: Methyl (2S,4S)-1-BOC-4-[(4,4-difluorocyclohexyl)(2,2-dimethylpropanoyl)amino]pyrrolidine-2-carboxylate Methyl (2S,4S)-1-BOC-4-[(4,4-difluorocyclohexyl)amino]pyrrolidine-2-carboxylate (1.03 g, 2.84 mmol) obtained in Step A was dissolved in DCE (5 mL) and TEA (5 mL) and DMAP (0.36 g, 2.84 mmol) were added thereto. Commercially available pivaloyl chloride (1.03 g, 8.52 mmol) was also added thereto. The reaction solution was heated to 90° C. and stirred for 24 hours. After the reaction was completed, the solvent was removed in vacuo and saturated NaHCO$_3$ aqueous solution was added. The solution was extracted with EtOAc. The extracted organic solution was washed with 1N HCl solution, dried over MgSO$_4$, concentrated in vacuo and purified by column chromatography (eluent: EtOAc/Hex=1/4) to give the title compound (1.04 g, 82%).
MS[M+H]=447 (M+1)

Step C: (4S)-1-BOC-4-[(4,4-difluorocyclohexyl)(2,2-dimethylpropanoyl)amino]-L-proline Methyl (2S,4S)-1-BOC-4-[(4,4-difluorocyclohexyl)(2,2-dimethylpropanoyl)amino]pyrrolidine-2-carboxylate (1.02 g, 2.32 mmol) obtained in Step B was reacted according to the same procedure as in the Step C of Example 1 to give the title compound (0.95 g, 95%).
MS[M+H]=433 (M+1)

Step D: (2S,4S)-1-BOC-4-[(4,4-difluorocyclohexyl)(2,2-dimethylpropanoyl)amino]-2-[(4-methylpiperazin-1-yl)carbonyl]pyrrolidine (4S)-1-BOC-4-[(4,4-difluorocyclohexyl)(2,2-dimethylpropanoyl)amino]-L-proline (0.95 g, 2.2 mmol) obtained in Step C was reacted according to the same procedure as in the Step D of Example 1 to give the title compound (1.05 g, 93%).
MS[M+H]=515 (M+1)

Step E: N-(4,4-difluorocyclohexyl)-2,2-dimethyl-N-{(3S,5S)-5-[(4-methylpiperazine-1-yl)carbonyl]pyrrolidin-3-yl}propanamide (2S,4S)-1-BOC-4-[(4,4-difluorocyclohexyl)(2,2-dimethylpropanoyl)amino]-2-[(4-methylpiperazin-1-yl)carbonyl]pyrrolidine (1.05 g, 2.04 mmol) obtained in Step D was reacted according to the same procedure as in the Step E of Example 1 to give the title compound (845 mg, 99.9%).
MS[M+H]=415 (M+1)

Step F: N-{(3S,5S)-1-{[(3S,4R)-1-tert-butyl-4-(4-chlorophenyl)pyrrolidine-3-yl]carbonyl}-5-[(4-methylpiperazin-1-yl)carbonyl]pyrrolidin-3-yl}-N-(4,4-difluorocyclohexyl)-2,2-dimethylpropanamide TFA salt N-(4,4-difluorocyclohexyl)-2,2-dimethyl-N-{(3S,5S)-5-[(4-methylpiperazin-1-yl)carbonyl]pyrrolidin-3-yl}propanamide (845 mg, 2.04 mmol) obtained in Step E and (3S,4R)-1-t-butyl-4-(4-chlorophenyl)pyrrolidine-3-carboxylic acid obtained in Preparation 12 were reacted according to the same procedure as in the Step F of Example 1 to give TFA salt of the title compound (1.18 g, 85%).
MS[M+H]=678 (M+1)
¹H NMR (500 MHz, DMSO-d$_6$, 140° C.) δ 7.42-7.30 (m, 4H), 4.80-4.70 (br, 1H), 3.91-3.82 (m, 1H), 3.82-3.55 (m, 10H), 3.39-3.28 (m, 2H), 3.24-3.12 (m, 1H), 3.02-2.85 (m, 4H), 2.65 (s, 3H), 2.39-2.30 (m, 1H), 2.22-2.13 (br, 1H), 2.13-1.81 (m, 6H), 1.63-1.56 (m, 1H), 1.56-1.48 (m, 1H), 1.38 (s, 9H), 1.17 (s, 9H)

Examples 27~31

Compounds of Preparations 1-23 were reacted according to the same procedure as Examples 1~4, 26 to give compounds of following Examples.

| Example | R2' | R3 | R5 | MS (M + 1) |
|---|---|---|---|---|
| 27 | 4-Cl | Me | Me | 636 |
| 28 | 4-Cl | Et | Me | 650 |
| 29 | 4-Cl | i-Pr | Me | 664 |
| 30 | 2,4-diF | Me | t-Bu | 680 |
| 31 | 4-Cl | Me | 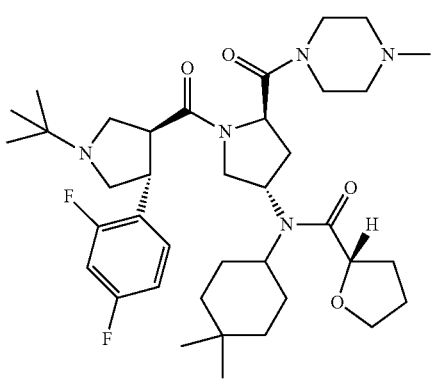 | 692 |

Example 32

(2S)—N-{(3S,5R)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide TFA salt TFA salt of Step A: Methyl (2R,4S)-1-BOC-4-[(4,4-dimethylcyclohexyl)amino]pyrrolidine-2-carboxylate Methyl (2R,4S)-1-Boc-4-aminopyrrolidine-2-carboxylate (1.07 g, 4.38 mmol) obtained in Preparation 2 and 4,4-dimethylcyclohexanone (0.66 g, 5.25 mmol) were dissolved in DCE (20 mL) and NaBH(OAc)₃ (1.39 g, 6.57 mmol) was added thereto at room temperature. The reaction solution was stirred for 4 hours at room temperature and was extracted with DCM (50 mL×2) and EtOAc. The extracted organic solution was washed with brine, dried over MgSO4, filterated and concentrated in vacuo. The obtained residue was purified by column chromatography (eluent, EtOAc/Hex=1/2) to give the title compound (1.16 g, 75%).

MS[M+H]=355 (M+1)

Step B: Methyl (2R,4S)-1-BOC-4-{(4,4-dimethylcyclohexyl)[(2S)-tetrahydrofuran-2-ylcarbonyl]amino}pyrrolidine-2-carboxylate Methyl (2R,4S)-1-BOC-4-[(4,4-dimethylcyclohexyl)amino]pyrrolidine-2-carboxylate (1.16 g, 3.27 mmol) obtained in Step A was reacted according to the same procedure as in the Step A of Example 3 to give the title compound (1.21 g, 82%).

MS[M+H]=453 (M+1)

Step C: (4S)-1-BOC-4-{(4,4-dimethylcyclohexyl)[(2S)-tetrahydrofuran-2-ylcarbonyl]amino}-D-proline Methyl (2R,4S)-1-BOC-4-{(4,4-dimethylcyclohexyl)[(2S)-tetrahydrofuran-2-ylcarbonyl]amino}pyrrolidine-2-carboxylate (1.21 g, 2.67 mmol) obtained in Step B was reacted according to the same procedure as in the Step C of Example 1 to give the title compound (1.14 g, 97%).

MS[M+H]=439 (M+1)

Step D: (2R,4S)-1-BOC-4-{(4,4-dimethylcyclohexyl)[(2S)-tetrahydrofuran-2-ylcarbonyl]amino}-2-[(4-methylpiperazin-1-yl)carbonyl]pyrrolidine (4S)-1-BOC-4-{(4,4-dimethylcyclohexyl)[2S)-tetrahydrofuran-2-ylcarbonyl]amino}-D-proline (1.14 g, 2.60 mmol) obtained in Step C was reacted according to the same procedure as in the Step D of Example 1 to give the title compound (1.29 g, 95%).

MS[M+H]=521 (M+1)

Step E: (2S)—N-(4,4-dimethylcyclohexyl)-N-{(3S,5R)-5-[(4-methylpiperazin-1-yl)carbonyl]pyrrolidin-3-yl}tetrahydrofuran-2-carboxamide (2R,4S)-1-BOC-4-{(4,4-dimethylcyclohexyl)[(2S)-tetrahydrofuran-2-ylcarbonyl]amino}-2-[(4-methylpiperazin-1-yl)carbonyl]pyrrolidine (1.29 g, 2.48 mmol) obtained in Step D was reacted according to the same procedure as in the Step E of Example 1 to give the title compound (1.04 g, 99.8%).

MS[M+H]=421 (M+1)

Step F: (2S)—N-{(3S,5R)-1-{[(3S,4R)-1-tert-butyl-4-(2,4-difluorophenyl)pyrrolidine-3-yl]carbonyl}-5-[(4-methylpiperazin-1-yl)carbonyl]pyrrolidin-3-yl}-N-(4,4-dimethylcyclohexyl)tetrahydrofuran-2-carboxamide TFA salt (2S)—N-(4,4-dimethylcyclohexyl)-N-{(3S,5R)-5-[(4-methylpiperazin-1-yl)carbonyl]pyrrolidin-3- yl}tetrahydrofuran-2-carboxamide (1.04 g, 2.47 mmol) obtained in Step E and (3S,4R)-1-t-butyl-4-(2,4-difluorophenyl)pyrrolidine-3-carboxylic acid obtained in Preparation 11 were reacted according to the same procedure as in the Step F of Example 1 to give the title compound (1.44 g, 85%).

MS[M+H]=686 (M+1)

$^1$H NMR (500 MHz, DMSO-$d_6$, 140° C.) δ 7.63-7.53 (m, 1H), 7.08-6.98 (m, 2H), 5.08-4.98 (br, 1H), 4.51 (dd, J=6.7, 6.15 Hz, 1H), 4.19-4.08 (m, 1H), 3.96-3.86 (m, 1H), 3.82-3.66 (m, 9H), 3.66-3.53 (m, 2H), 3.53-3.42 (m, 1H), 3.34 (dd, J=11.6, 11.0 Hz, 1H), 3.23-3.13 (m, 1H), 3.13-3.00 (m, 4H), 2.74 (s, 3H), 2.66-2.56 (m, 1H), 2.08-1.98 (m, 1H), 1.98-1.88 (m, 1H), 1.88-1.78 (m, 2H), 1.78-1.63 (m, 1H), 1.63-1.49 (m, 1H), 1.45-1.24 (m, 7H), 1.38 (s, 9H), 0.90 (s, 6H)

Examples 33~40

Compounds of Preparations 1-23 were reacted according to the same procedure as Examples 1~4 to give compounds of following Examples.

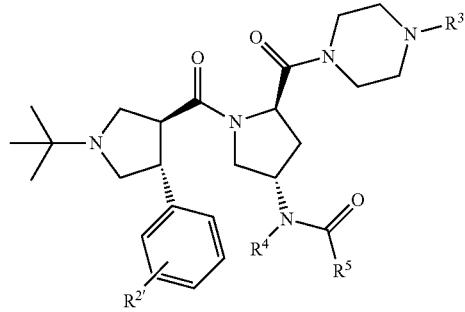

| Example | R²' | R³ | R⁴ | R⁵ | MS (M+1) |
|---|---|---|---|---|---|
| 33 | 2,4-diF | Me | cis-4-Me-c-Hex | t-Bu | 658 |
| 34 | 4-Cl | Me | 4,4-diMe-c-Hex | ![tetrahydrofuran] | 684 |
| 35 | 4-Cl | Me | cis-4-Me-c-Hex | ![tetrahydrofuran] | 670 |
| 36 | 4-Cl | Me | cis-4-Me-c-Hex | C(CH₃)₂CH₂OH | 672 |
| 37 | 4-Cl | Me | cis-4-Me-c-Hex | Me | 614 |
| 38 | 2,4-diF | Me | cis-4-Me-c-Hex | Me | 616 |
| 39 | 4-Cl | i-Pr | cis-4-Me-c-Hex | Me | 642 |
| 40 | 4-Cl | Me | cis-4-Me-c-Hex | ![tetrahydrofuran] | 670 |

Example 41

(2S)—N-{(3S,5S)-1-{[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide TFA salt TFA salt of

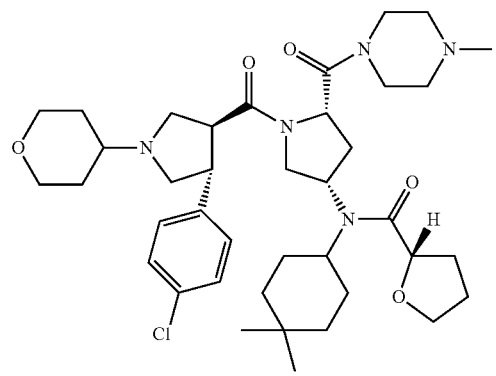

Step A: 1-BOC-(3R,4S)-3-(4-chlorophenyl)-4-({(2S,4S)-4-{(4,4-dimethylcyclohexyl)[(2S)-tetrahydrofuran-2-ylcarbonyl]amino}-2-[(4-methylpiperazin-1-yl)carbonyl]pyrrolidin-1-yl}-carbonyl)pyrrolidine (2S)—N-(4,4-dimethylcyclohexyl)-N-{(3S,5S)-5-[(4-methylpiperazin-1-yl)carbonyl]pyrrolidin-3-yl}tetrahydrofuran-2-carboxamide (903 mg, 2.15 mmol) obtained in Step D of Example 3 was dissolved in DMF (5 mL). After DIPEA (0.94 mL, 5.37 mmol) was added thereto, (3S,4R)-1-BOC-4-(4-chlorophenyl)pyrrolidine-3-carboxylic acid (0.70 g, 2.15 mmol) obtained in Preparation 14 and HBTU (0.81 g, 2.15 mmol) were added thereto. The reaction solution was stirred for 2 hours and concentrated in vacuo. The residue was diluted with EtOAc and washed with saturated NaHCO₃ aqueous solution. The extracted organic solution was dried over MgSO₄ and concentrated in vacuo. The obtained residue was purified by column chromatography (eluent, DCM/MeOH=15/1) to give the title compound (1.33 g, 85%).

MS[M+H]=728 (M+1)

Step B: (2S)—N-{(3S,5S)-1-{[(3S,4R)-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide 1-BOC-(3R,4S)-3-(4-chlorophenyl)-4-({(2S,4S)-4-{(4,4-dimethylcyclohexyl)[(2S)-tetrahydrofuran-2-ylcarbonyl]amino}-2-[(4-methylpiperazin-1-yl)carbonyl]pyrrolidin-1-yl}carbonyl)pyrrolidine (1.33 g, 1.83 mmol) obtained in Step A was dissolved in DCM (1 mL) and 4M HCl (1 mL) was added dropwise thereto. The reaction solution was stirred for 1 hour at room temperature and concentrated in vacuo to give the title compound (1.14 g, 99.8%).

MS[M+H]=628 (M+1)

Step C: (2S)—N-{(3S,5S)-1-{[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide TFA salt (2S)—N-{(3S,5S)-1-{[3S,4R)-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide (1.14 g, 1.81 mmol) obtained in Step B and tetrahydro-4H-pyran-4-one (0.34 mL, 3.62 mmol) were dissolved in DCE (10 mL) and NaBH(OAc)$_3$ (0.58 g, 2.74 mmol) was added thereto at room temperature. After the reaction solution was stirred for 2 hours at room temperature, saturated NaHCO$_3$ aqueous solution was added and the solution was extracted with EtOAc. The extracted organic solution was washed with brine, dried over MgSO$_4$, filtered and concentrated in vacuo. The obtained residue was purified by HPLC to give TFA salt of the title compound (1.16 g, 90%).

MS[M+H]=712 (M+1)

$^1$H NMR (500 MHz, DMSO-d$_6$, 140° C.) δ 7.42-7.29 (m, 4H), 4.81-4.70 (br, 1H), 4.50 (dd, J=6.75, 6.7 Hz, 1H), 3.99-3.89 (m, 2H), 3.89-3.54 (m, 12H), 3.54-3.20 (m, 7H), 3.16-2.94 (m, 4H), 2.73 (s, 3H), 2.43-2.30 (m, 1H), 2.27-2.12 (br, 1H), 2.07-1.94 (m, 3H), 1.94-1.76 (m, 4H), 1.74-1.62 (m, 3H), 1.48-1.20 (m, 6H), 0.93, 0.90 (2s, 6H)

Example 42

(2S)—N-{(3S,5S)-1-{[(3S,4R)-4-(4-chlorophenyl)-1-cyclopropyl pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide TFA salt TFA salt of

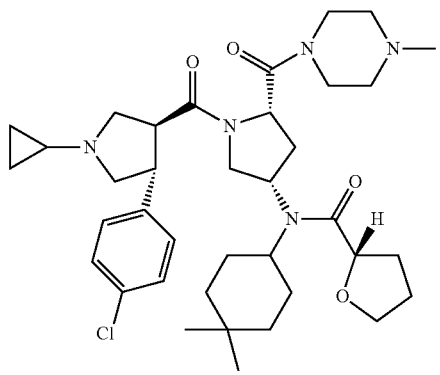

(2S)—N-{(3S,5S)-1-{[3S,4R)-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide (1.14 g, 1.81 mmol) obtained in Step B of Example 41 was dissolved in DCE (20 mL). 1-ethoxycyclopropoxytrimethylsilane (0.47 g, 2.70 mmol) and NaBH$_3$CN (228 mg, 3.63 mmol) were added thereto. After catalytic amount of acetic acid was added, the reaction solution was stirred for 2 hours at 80° C. After the reaction was completed, the solution was concentrated in vacuo. The residue was diluted with EtOAc and washed with saturated NaHCO$_3$ aqueous solution. The extracted organic solution was dried over MgSO$_4$ and concentrated in vacuo. The obtained residue was purified by HPLC to give TFA salt of the title compound (1.03 g, 85%).

MS[M+H]=668 (M+1)

$^1$H NMR (500 MHz, DMSO-d$_6$, 140° C.) δ 7.44-7.24 (m, 4H), 4.80-4.71 (br, 1H), 4.29-4.20 (m, 1H), 3.95-3.38 (m, 13H), 3.38-3.20 (m, 2H), 3.20-2.89 (m, 6H), 2.74, 2.72 (2s, 3H), 2.64-2.49 (m, 1H), 2.42-2.34 (m, 1H), 2.25-2.10 (m, 1H), 2.10-1.96 (m, 1H), 1.96-1.76 (m, 3H), 1.76-1.62 (m, 2H), 1.62-1.46 (m, 3H), 1.46-1.20 (m, 3H), 0.93, 0.90 (2s, 6H), 0.81-0.56 (m, 3H)

Example 43

(2S)—N-{(3S,5S)-1-{[(3S,4R)-4-(4-chlorophenyl)-1-(6-methylpyridazin-3-yl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide TFA salt TFA salt of

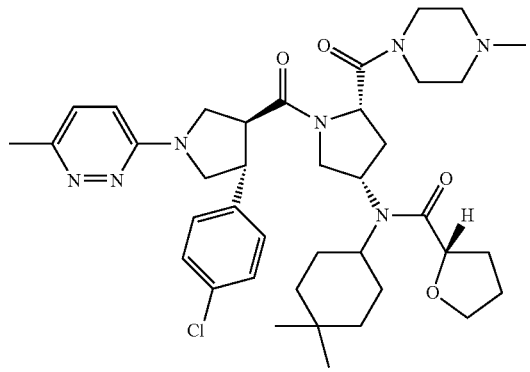

(2S)—N-(4,4-dimethylcyclohexyl)-N-{(3S,5S)-5-[(4-methylpiperazin-1-yl)carbonyl]pyrrolidin-3-yl}tetrahydrofuran-2-carboxamide (903 mg, 2.15 mmol) obtained in Step D of Example 3 was dissolved in DMF (5 mL). DIPEA (0.94 mL, 5.38 mmol) was added thereto and (3S,4R)-4-(4-chlorophenyl)-1-(6-methylpyridazin-3-yl)pyrrolidine-3-carboxylic acid (0.68 g, 2.15 mmol) obtained in Preparation 17 and HBTU (0.82 g, 2.15 mmol) were added in turn. The reaction solution was stirred for 2 hours at room temperature and concentrated in vacuo. The residue was dissolved with EtOAc and washed with saturated NaHCO$_3$ aqueous solution and water. The extracted organic solution was dried over MgSO$_4$ and concentrated in vacuo. The residue was purified by HPLC to give TFA salt of the title compound (1.31 g, 85%).

MS[M+H]=668 (M+1)

$^1$H NMR (500 MHz, DMSO-d$_6$, 140° C.) δ 7.55-7.49 (m, 1H), 7.43-7.30 (m, 4H), 7.29-7.23 (m, 1H), 4.84-4.73 (br, 1H), 4.55 (dd, J=6.75, 6.1 Hz, 1H), 4.14-3.79 (m, 5H), 3.79-3.62 (m, 7H), 3.62-3.32 (m, 4H), 3.22-3.03 (m, 4H), 2.78 (s, 3H), 2.52-2.42 (m, 1H), 2.46 (s, 3H), 2.21-2.10 (br, 1H), 1.97-1.86 (m, 1H), 1.82-1.51 (m, 5H), 1.51-1.12 (m, 6H), 0.95, 0.92 (2s, 6H)

Example 44

(2S)—N-{(3S,5S)-1-{[(3S,4R)-4-(2,4-difluorophenyl)-1-(6-chloropyridazin-3-yl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide TFA salt TFA salt of

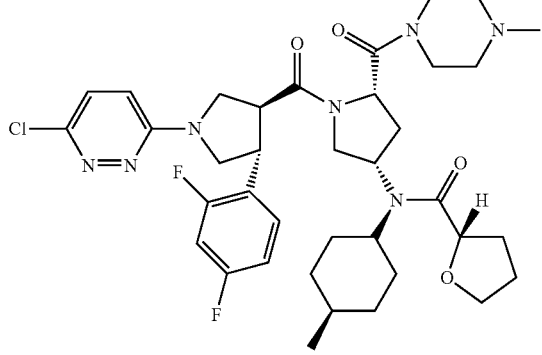

(2S)—N-(cis-4-methylcyclohexyl)-N-{(3S,5S)-5-[(4-methylpiperazin-1-yl)carbonyl]pyrrolidin-3-yl}tetrahydrofuran-2-carboxamide (0.76 g, 1.87 mmol) obtained in Step E of Example 16 and (3S,4R)-4-(2,4-difluorophenyl)-1-(6-chloropyridazin-3-yl)pyrrolidine-3-carboxylic acid obtained in Preparation 19 were reacted according to the same procedure as in the Step F of Example 1 to give the title compound (1.20 g, 88%).

MS[M+H]=728 (M+1)

$^1$H NMR (500 MHz, DMSO-d$_6$, 140° C.) δ 7.51-7.42 (m, 1H), 7.37 (d, 1H), 7.05-6.94 (m, 3H), 4.80-4.72 (br, 1H), 4.53 (dd, J=6.75, 6.1 Hz, 1H), 4.08-3.87 (m, 5H), 3.80-3.66 (m, 7H), 3.63-3.48 (m, 4H), 3.22-2.93 (m, 4H), 2.79 (s, 3H), 2.42-2.36 (m, 1H), 2.25-2.16 (br, 1H), 2.10-2.01 (m, 1H), 1.98-1.76 (m, 6H), 1.64-1.47 (m, 4H), 1.40-1.30 (m, 2H), 0.98 (d, 3H)

Example 45

(2S)—N-{(3S,5S)-1-{[(3S,4R)-4-(2,4-difluorophenyl)-1,6-dihydropyridazin-3-ylpyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide TFA salt TFA salt of

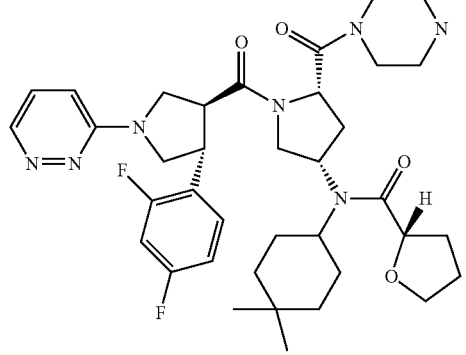

(2S)—N-(4,4-dimethylcyclohexyl)-N-{(3S,5S)-5-[(4-methylpiperazin-1-yl)carbonyl]pyrrolidin-3-yl}tetrahydrofuran-2-carboxamide (903 mg, 2.15 mmol) obtained in Step D of Example 3 and (3S,4R)-4-(4-chlorophenyl)-1-(1,6-dihydropyridazin-3-yl)pyrrolidine-3-carboxylic acid obtained in Preparation 21 were reacted according to the same procedure as in the Step F of Example 1 to give the title compound (1.34 g, 88%).

MS[M+H]=708 (M+1)

$^1$H NMR (500 MHz, DMSO-d$_6$, 140° C.) δ 8.57-8.52 (d, 1H), 7.57-7.43 (m, 2H), 7.22-7.14 (m, 1H), 7.08-6.97 (m, 2H), 4.84-4.72 (br, 1H), 4.56-4.51 (m, 1H), 4.15-4.01 (m, 3H), 4.01-3.88 (m, 2H), 3.83-3.45 (m, 11H), 3.25-3.07 (m, 4H), 2.81 (s, 3H), 2.46-2.35 (m, 1H), 2.27-2.14 (br, 1H), 2.11-2.01 (m, 1H), 1.99-1.74 (m, 6H), 1.65-1.47 (m, 4H), 1.40-1.30 (m, 1H), 0.94, 0.92 (2s, 6H)

Example 46

(2S)—N-{(3S,5S)-1-{[(3S,4R)-4-(4-chlorophenyl)-1-phenylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide TFA salt TFA salt of

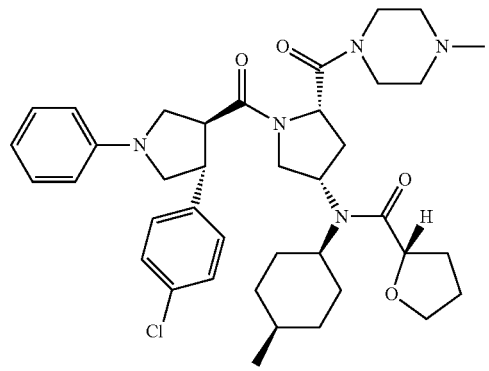

Step A: 1-BOC-(3R,4S)-3-(4-chlorophenyl)-4-({(2S,4S)-4-{(cis-4-methylcylcohexyl)[(2S)-tetrahydrofuran-2-ylcarbonyl]amino}-2-[(4-methylpiperazin-1-yl)carbonyl]pyrrolidin-1-yl}carbonyl)pyrrolidine (2S)—N-(cis-4-methylcyclohexyl)-N-{(3S,5S)-5-[(4-methylpiperazin-1-yl)carbonyl]pyrrolidin-3-yl}tetrahydrofuran-2-carboxamide (0.76 g, 1.87 mmol) obtained in Step E of Example 16 and (3S,4R)-1-BOC-4-(4-chlorophenyl)pyrrolidine-3-carboxylic acid obtained in Preparation 14 were reacted according to the same procedure as in the Step F of Example 1 to give the title compound (1.18 g, 88%).

MS[M+H]=714 (M+1)

Step B: (2S)—N-{(3S,5S)-{[(3S,4R)-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide 1-BOC-(3R,4S)-3-(4-chlorophenyl)-4-({(2S,4S)-4-{(cis-4-methylcyclohexyl)[(2S)-tetrahydrofuran-2-ylcarbonyl]amino}-2-[(4-methylpiperazin-1-yl)carbonyl]pyrrolidin-1-yl}-carbonyl)pyrrolidine (1.18 g, 1.65 mmol) obtained in Step A was dissolved in DCM (1 mL). 4M HCl (1 mL) was added dropwise thereto. The reaction solution was stirred for 1 hour at room temperature, concentrated in vacuo to give the title compound (1.01 g, 99.8%).

MS[M+H]=614 (M+1)

Step C: (2S)—N-{(3S,5S)-1-{[(3S,4R)-4-(4-chlorophenyl)-1-phenylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide TFA salt ((2S)—N-{(3S,5S)-1-{[(3S,4R)-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide (1.01 g, 1.64 mmol) obtained in Step B was dissolved in toluene (10 mL). Sodium t-butoxide (0.18 g, 1.87 mmol), 2-(di-t-butylphosphino)biphenyl (42 mg, 0.14 mmol), Tris(dibenzylideneacetone)-dipalladium(0) (80 mg, 0.09 mmol) and bromobenzene (29 mg, 1.87 mmol) were added thereto and stirred for 10 hours at 110° C. After the reaction was completed, solid like material was filtered from using the Celite. The reaction solution was diluted with EtOAc and washed with saturated NaHCO$_3$ aqueous solution. The organic layer was dried over MgSO$_4$ and concentrated in vacuo. The residue was purified by HPLC to give the title compound (0.89 g, 78%).

MS[M+H]=690 (M+1)

$^1$H NMR (500 MHz, DMSO-d$_6$, 140° C.) δ 7.75-7.64 (m, 1H), 7.62-7.52 (m, 2H), 7.52-7.40 (m, 2H), 7.40-7.27 (m, 3H), 7.24-7.10 (m, 1H), 4.92-4.83 (br, 1H), 4.56-4.45 (m, 1H), 4.15-3.80 (m, 5H), 3.80-3.44 (m, 11H), 3.25-3.07 (m, 4H), 2.77 (s, 3H), 2.46-2.35 (m, 1H), 2.27-2.14 (m, 1H), 2.11-2.01 (m, 1H), 1.99-1.74 (m, 6H), 1.65-1.47 (m, 4H), 1.41-1.29 (m, 2H), 0.98 (d, 3H)

Examples 47~73

Compounds of Preparations 1-23 were reacted according to the same procedure as Examples 1~4, 41~46 to give compounds of following Examples.

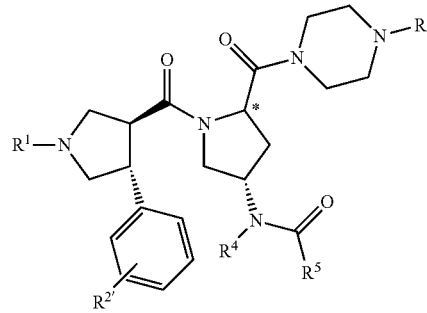

| Ex. | R$^1$ | R$^{2'}$ | R$^3$ | R$^4$ | R$^5$ | * | MS (M+1) |
|---|---|---|---|---|---|---|---|
| 47 | (tetrahydropyran-4-yl) | 2,4-diF | i-Pr | 4,4-diMe-c-Hex | (3-Me-tetrahydrofuran-3-yl, H) | S | 742 |
| 48 | (tetrahydrothiopyran-4-yl) | 2,4-diF | i-Pr | 4,4-diMe-c-Hex | (3-Me-tetrahydrofuran-3-yl, H) | S | 758 |

-continued

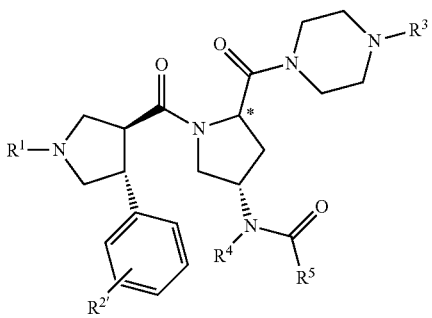

| Ex. | R$^1$ | R$^{2'}$ | R$^3$ | R$^4$ | R$^5$ | * | MS (M+1) |
|---|---|---|---|---|---|---|---|
| 49 | (tetrahydropyran-4-yl) | 4-Cl | Me | 4,4-diMe-c-Hex | C(CH$_3$)$_2$CH$_2$OH | S | 714 |
| 50 | (tetrahydropyran-4-yl) | 4-Cl | Me | 4,4-diF-c-Hex | t-Bu | S | 706 |
| 51 | (tetrahydropyran-4-yl) | 4-Cl | Me | 4,4-diF-c-Hex | (3-Me-tetrahydrofuran-3-yl, H) | S | 720 |
| 52 | (tetrahydropyran-4-yl) | 2,4-diF | i-Pr | 4,4-diMe-c-Hex | (3-Me-tetrahydrofuran-3-yl, H) | R | 742 |
| 53 | (tetrahydropyran-4-yl) | 2,4-diF | Me | cis-4-Me-c-Hex | t-Bu | S | 686 |
| 54 | (tetrahydropyran-4-yl) | 4-Cl | Me | cis-4-Me-c-Hex | Me | R | 642 |
| 55 | c-Pr | 4-Cl | Me | 4,4-diMe-c-Hex | (3-Me-tetrahydrofuran-3-yl, H) | R | 668 |
| 56 | c-Pr | 4-Cl | Me | cis-4-Me-c-Hex | (3-Me-tetrahydrofuran-3-yl, H) | S | 654 |
| 57 | c-Pr | 4-Cl | Me | cis-4-Me-c-Hex | (3-Me-tetrahydrofuran-3-yl, H) | R | 654 |
| 58 | c-Pr | 4-Cl | Me | 4,4-diMe-c-Hex | C(CH$_3$)$_2$CH$_2$OH | S | 670 |
| 59 | c-Pr | 4-Cl | Me | cis-4-Me-c-Hex | C(CH$_3$)$_2$CH$_2$OH | S | 656 |
| 60 | c-Pr | 2,4-diF | Me | cis-4-Me-c-Hex | C(CH$_3$)$_2$CH$_2$OH | S | 658 |
| 61 | c-Pr | 4-Cl | Me | 4,4-diF-c-Hex | C(CH$_3$)$_2$CH$_2$OH | S | 678 |

-continued

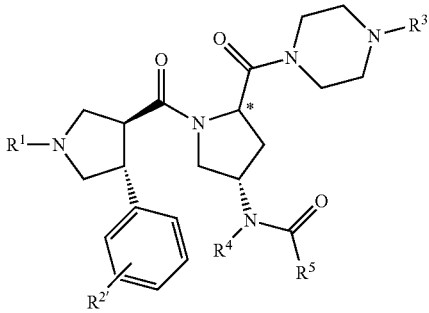

| Ex. | R¹ | R²' | R³ | R⁴ | R⁵ | * | MS (M+1) |
|---|---|---|---|---|---|---|---|
| 62 | i-Pr | 4-Cl | Me | cis-4-Me-c-Hex | Me | R | 600 |
| 63 | 6-Me-pyridazin-3-yl | 4-Cl | Me | 4,4-diMe-c-Hex | t-Bu | S | 706 |
| 64 | pyridin-2-yl | 4-Cl | Me | 4,4-diMe-c-Hex | t-Bu | S | 691 |
| 65 | pyridin-2-yl | 4-Cl | Me | 4,4-diMe-c-Hex | (S)-tetrahydrofuran-2-yl | S | 705 |
| 66 | pyridazin-3-yl | 2,4-diF | Me | cis-4-Me-c-Hex | (S)-tetrahydrofuran-2-yl | S | 694 |
| 67 | pyrimidin-2-yl | 4-Cl | Me | 4,4-diMe-c-Hex | t-Bu | S | 692 |
| 68 | pyridin-2-yl | 2,4-diF | Me | cis-4-Me-c-Hex | (S)-tetrahydrofuran-2-yl | S | 693 |
| 69 | 5-CN-pyridin-2-yl | 4-Cl | Me | cis-4-Me-c-Hex | (S)-tetrahydrofuran-2-yl | S | 716 |
| 70 | thiazol-2-yl | 4-Cl | Me | 4,4-diMe-c-Hex | t-Bu | S | 697 |
| 71 | 2-Me-phenyl | 4-Cl | Me | cis-4-Me-c-Hex | (S)-tetrahydrofuran-2-yl | S | 704 |
| 72 | 1-Me-6-oxo-pyridazin-3-yl | 4-Cl | Me | cis-4-Me-c-Hex | (S)-tetrahydrofuran-2-yl | S | 722 |

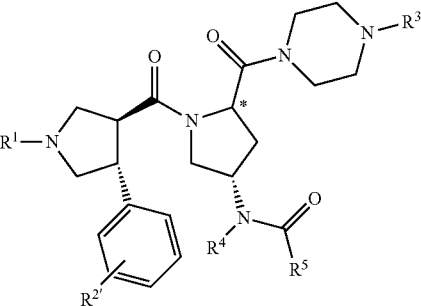

| Ex. | R¹ | R²' | R³ | R⁴ | R⁵ | * | MS (M+1) |
|---|---|---|---|---|---|---|---|
| 73 | 6-oxo-1H-pyridazin-3-yl | 4-Cl | Me | cis-4-Me-c-Hex | (S)-tetrahydrofuran-2-yl | S | 708 |

Example 48

TFA Salt

¹H NMR (500 MHz, DMSO-d₆, 140° C.) δ 7.61-7.48 (m, 1H), 7.08-6.95 (m, 2H), 4.79-4.69 (br, 1H), 4.51 (dd, J=6.15, 6.1 Hz, 1H), 4.04-3.94 (m, 1H), 3.94-3.81 (m, 2H), 3.81-3.56 (m, 9H), 3.54-3.45 (m, 1H), 3.45-3.33 (m, 2H), 3.33-3.23 (m, 2H), 3.23-3.11 (m, 3H), 3.11-2.98 (m, 2H), 2.78-2.70 (m, 2H), 2.70-2.61 (m, 2H), 2.44-2.30 (m, 3H), 2.26-2.13 (br, 1H), 2.08-1.99 (m, 1H), 1.96-1.64 (m, 7H), 1.45-1.20 (m, 6H), 1.27, 1.26 (2s, 6H), 0.92, 0.90 (2s, 6H)

Example 56

TFA Salt

1H NMR (500 MHz, DMSO-d₆, 140° C.) δ 7.43-7.24 (m, 4H), 4.81-4.70 (br, 1H), 4.28-4.20 (m, 1H), 3.95-3.38 (m, 13H), 3.38-3.19 (m, 2H), 3.19-2.89 (m, 6H), 2.74, 2.72 (2s, 3H), 2.64-2.50 (m, 1H), 2.42-2.34 (m, 1H), 2.26-2.10 (m, 1H), 2.10-1.97 (m, 1H), 1.97-1.77 (m, 3H), 1.77-1.62 (m, 2H), 1.62-1.46 (m, 3H), 1.46-1.20 (m, 4H), 0.95 (d, 3H), 0.81-0.56 (m, 3H)

Example 61

TFA Salt

¹H NMR (500 MHz, DMSO-d₆, 140° C.) δ 7.36-7.28 (m, 4H), 4.79-4.70 (m, 1H), 3.88-3.57 (m, 8H), 3.57-3.46 (m, 2H), 3.41 (s, 2H), 3.32-3.16 (m, 3H), 3.16-2.96 (m, 4H), 2.75 (s, 3H), 2.60-2.49 (m, 1H), 2.42-2.32 (m, 1H), 2.24-2.12 (br, 1H), 2.12-1.82 (m, 6H), 1.66-1.58 (m, 1H), 1.58-1.50 (m, 1H), 1.28-1.17 (m, 1H), 1.14 (s, 6H), 0.80-0.70 (m, 2H), 0.70-0.62 (m, 2H)

Example 63

TFA Salt

¹H NMR (500 MHz, DMSO-d₆, 140° C.) δ 7.53-7.48 (m, 1H), 7.40-7.28 (m, 4H), 7.28-7.22 (m, 1H), 4.82-4.70 (br, 1H), 4.12-4.02 (m, 2H), 4.02-3.92 (m, 1H), 3.88-3.79 (m,

1H), 3.79-3.62 (m, 7H), 3.62-3.55 (m, 1H), 3.55-3.46 (m, 1H), 3.42-3.30 (m, 1H), 3.22-3.02 (m, 4H), 2.77 (s, 3H), 2.52-2.42 (m, 1H), 2.46 (s, 3H), 2.20-2.09 (br, 1H), 1.97-1.86 (m, 1H), 1.82-1.70 (br, 1H), 1.51-1.12 (m, 6H), 1.17 (s, 9H), 0.95, 0.92 (2s, 6H)

Example 64

TFA Salt $^1$H NMR (500 MHz, DMSO-d$_6$, 140° C.) δ 8.5-8.0 (m, 1H), 7.64-7.56 (m, 1H), 7.42-7.25 (m, 4H), 6.69-6.60 (m, 2H), 4.81-4.70 (br, 1H), 4.04-3.92 (m, 3H), 3.87-3.66 (m, 6H), 3.66-3.45 (m, 4H), 3.45-3.32 (m, 1H), 3.24-3.04 (m, 4H), 2.78 (s, 3H), 2.52-2.40 (m, 1H), 2.20-2.07 (br, 1H), 1.98-1.86 (m, 1H), 1.84-1.70 (br, 1H), 1.52-1.12 (m, 6H), 1.17 (s, 9H), 0.94, 0.92 (2s, 6H)

Example 66

TFA Salt $^1$H NMR (500 MHz, DMSO-d$_6$, 140° C.) δ 8.55-8.50 (d, 1H), 7.56-7.43 (m, 2H), 7.20-7.13 (m, 1H), 7.08-6.96 (m, 2H), 4.82-4.71 (br, 1H), 4.56-4.50 (m, 1H), 4.15-4.01 (m, 3H), 4.01-3.87 (m, 2H), 3.83-3.45 (m, 11H), 3.25-3.07 (m, 4H), 2.80 (s, 3H), 2.46-2.35 (m, 1H), 2.27-2.14 (br, 1H), 2.11-2.01 (m, 1H), 1.99-1.74 (m, 6H), 1.65-1.47 (m, 4H), 1.41-1.29 (m, 2H), 0.97 (d, 3H)

Example 74

(2S)—N-{(3S,5S)-1-{[(3R,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide TFA salt TFA salt of

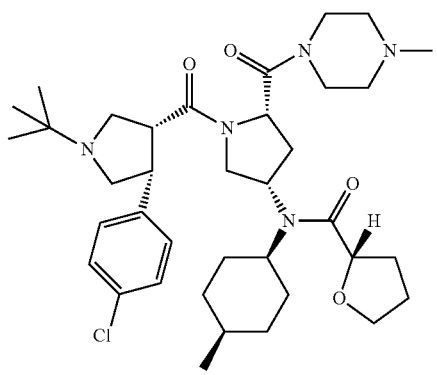

2S)—N-(cis-4-methylcyclohexyl)-N-{(3S,5S)-5-[(4-methylpiperazin-1-yl)carbonyl]pyrrolidin-3-yl}tetrahydrofuran-2-carboxamide (0.76 g, 1.87 mmol) obtained in Step E of Example 16 and (3R,4R)-1-t-butyl-4-(4-chlorophenyl)pyrrolidine-3-carboxylic acid obtained in Preparation 15 were reacted according to the same procedure as Step F of Example 1 to give the title compound (1.10 g, 88%).

MS[M+H]=670 (M+1)

$^1$H NMR (500 MHz, DMSO-d$_6$, 140° C.) δ 7.42-7.21 (m, 4H), 4.70-4.19 (m, 2H), 3.90-3.78 (m, 1H), 3.78-3.68 (m, 3H), 3.68-3.48 (m, 6H), 3.42-2.95 (m, 5H), 2.87 (s, 3H), 2.70-2.54 (m, 4H), 2.34-2.13 (m, 2H), 2.08-1.99 (m, 1H), 1.95-1.78 (m, 5H), 1.75-1.65 (m, 1H), 1.61-1.47 (m, 4H), 1.42 (s, 9H), 1.37-1.20 (m, 3H), 1.00 (s, 3H)

Example 75

(2S)—N-{(3S,5S)-1-{[(3S,4S)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide TFA salt TFA salt of

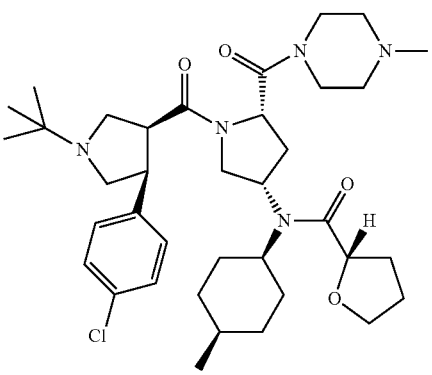

(2S)—N-(cis-4-methylcyclohexyl)-N-{(3S,5S)-5-[(4-methylpiperazin-1-yl)carbonyl]pyrrolidin-3-yl}tetrahydrofuran-2-carboxamide (0.76 g, 1.87 mmol) obtained in Step E of Example 16 and (3S,4S)-1-t-butyl-4-(4-chlorophenyl)pyrrolidine-3-carboxylic acid obtained in Preparation 16 were reacted according to the same procedure as Step F of Example 1 to give the title compound (1.10 g, 88%).

MS[M+H]=670 (M+1)

$^1$H NMR (500 MHz, DMSO-d$_6$, 140° C.) δ 7.39-7.28 (m, 4H), 4.48-4.43 (m, 1H), 4.41-4.35 (m, 1H), 3.92-3.82 (m, 2H), 3.82-3.73 (m, 2H), 3.73-3.59 (m, 8H), 3.50-3.36 (m, 2H), 3.25-3.18 (m, 1H), 3.18-3.04 (m, 4H), 2.77 (s, 3H), 2.29-2.19 (m, 1H), 2.10-1.99 (m, 2H), 1.95-1.79 (m, 5H), 1.79-1.69 (m, 1H), 1.62-1.46 (m, 4H), 1.41 (s, 9H), 1.39-1.25 (m, 3H), 1.00 (d, 3H)

Example 76

(2S)—N-{(3R,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide TFA salt TFA salt of

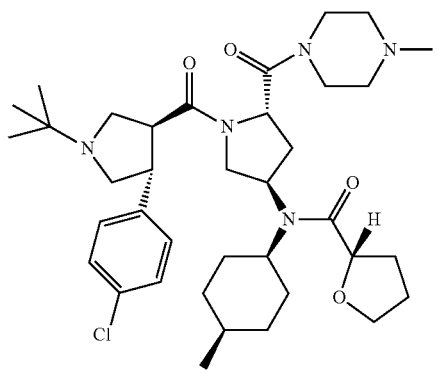

Step A: Methyl (2S,4R)-1-BOC-4-[(cis-4-methylcyclohexyl)amino]pyrrolidine-2-carboxylate Methyl (2S,4R)-1-Boc-4-aminopyrrolidine-2-carboxylate (1.07 g, 4.38 mmol) obtained in Preparation 3 was reacted according to the same procedure as Step A of Example 16 to give the title compound (0.84 g, 57%).
MS[M+H]=341 (M+1)

Step B: Methyl (2S,4R)-1-BOC-4-{(cis-4-methylcyclohexyl)[(2S)-tetrahydrofuran-2-ylcarbonyl]amino}pyrrolidine-2-carboxylate Methyl (2S,4R)-1-BOC-4-[cis-4-methylcyclohexyl)amino]pyrrolidine-2-carboxylate (0.84 g, 2.49 mmol) obtained in Step A was reacted according to the same procedure as Step A of Example 3 to give the title compound (0.92 g, 87%).
MS[M+H]=439 (M+1)

Step C: (4R)-1-BOC-4-{(cis-4-methylcyclohexyl)[(2S)-tetrahydrofuran-2-ylcarbonyl]amino}-L-proline Methyl (2S,4R)-1-BOC-4-{(cis-4-methylcyclohexyl)[(2S)-tetrahydrofuran-2-ylcarbonyl]amino}pyrrolidine-2-carboxylate (0.92 g, 2.10 mmol) obtained in Step B was reacted according to the same procedure as Step C of Example 1 to give the title compound (0.85 g, 95%).
MS[M+H]=425 (M+1)

Step D: (2S,4R)-1-BOC-4-{(cis-4-methylcyclohexyl)[(2S)-tetrahydrofuran-2-ylcarbonyl]amino}-2-[(4-methylpiperazin-1-yl)carbonyl]pyrrolidine (4R)-1-BOC-4-{(cis-4-methylcyclohexyl)[(2S)-tetrahydrofuran-2-ylcarbonyl]amino}-L-proline (0.85 g, 2.00 mmol) obtained in Step C was reacted according to the same procedure as Step D of Example 1 to give the title compound (0.95 g, 94%)
MS[M+H]=507 (M+1).

Step E: (2S)—N-(cis-4-methylcyclohexyl)-N-{(3R,5S)-5-[(4-methylpiperazin-1-yl)carbonyl]pyrrolidin-3-yl}tetrahydrofuran-2-carboxamide (2S,4R)-1-BOC-4-{(cis-4-methylcyclohexyl)[(2S)-tetrahydrofuran-2-ylcarbonyl]amino}-2-[(4-methylpiperazin-1-yl)carbonyl]pyrrolidine (0.95 g, 1.87 mmol) obtained in Step D was reacted according to the same procedure as Step E of Example 1 to give the title compound (0.76 g, 99.8%).
MS[M+H]=407 (M+1)

Step F: (2S)—N-[(3R,5S)-1{[(3S,4R)-1-tert-butyl-4-(4-chlorophenyl)pyrrolidin-3-yl]carbonyl}-5-[(4-methylpiperazin-1-yl)carbonyl]pyrrolidin-3-yl]-N-(cis-4-methylcyclohexyl)tetrahydrofuran-2-carboxamide TFA salt (2S)—N-(cis-4-methylcyclohexyl)-N-{(3R,5S)-5-[(4-methylpiperazin-1-yl)carbonyl]pyrrolidin-3-yl}tetrahydrofuran-2-carboxamide (0.76 g, 1.87 mmol) obtained in Step E and (3S,4R)-1-t-butyl-4-(4-chlorophenyl)pyrrolidine-3-carboxylic acid obtained in Preparation 12 were reacted according to the same procedure as Step F of Example 1 to give the title compound (1.10 g, 88%).
MS[M+H]=670 (M+1)
$^1$H NMR (500 MHz, DMSO-$d_6$, 140° C.) δ 7.37-7.29 (m, 4H), 5.06-4.98 (br, 1H), 4.52-4.47 (m, 1H), 4.32-3.40 (m, 12H), 3.36-3.26 (m, 2H), 3.20-3.07 (m, 5H), 2.80 (s, 3H), 2.59-2.48 (m, 1H), 2.08-1.98 (m, 1H), 1.98-1.90 (m, 1H), 1.90-1.74 (m, 6H), 1.61-1.46 (m, 4H), 1.39 (s, 9H), 1.44-1.24 (m, 3H), 0.94 (d, 3H)

The compounds of the Examples synthesized by the procedure of Reaction Scheme B are as follows:

Example 77

(2S)—N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(2,4-difluorophenyl)tetrahydrofuran-2-carboxamide TFA salt TFA salt of

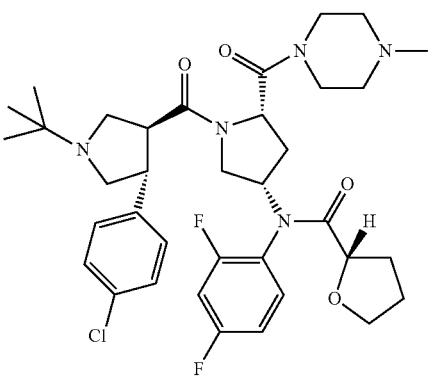

Step A: (2S,4S)-1-Boc-4-azidopyrrolidine-2-carboxylic acid

Methyl (2S,4S)-1-Boc-4-azidopyrrolidine-2-carboxylate (10 g, 37 mmol) obtained in Step D of Preparation 1 was dissolved in MeOH (100 mL) and water (100 mL). LiOH (2.5 g, 111 mmol) was added thereto. The reaction solution was stirred for 3 hours at room temperature, concentrated in vacuo and acidified with 1N HCl. The solution was extracted with EtOAc. The extracted organic solution was washed with brine, dried over MgSO$_4$ and concentrated in vacuo to give the title compound (9.5 g, 95%).

MS[M+H]=257 (M+1)

Step B: (2S,4S)-1-Boc-4-azido-2-[(4-methylpiperazin-1-yl)carbonyl]pyrrolidine (2S,4S)-1-Boc-4-azidopyrrolidine-2-carboxylic acid (9.5 g, 35 mmol) obtained in Step A was dissolved in DMF (30 mL). After DIPEA (1.15 mL, 6.70 mmol) was added thereto, 1-methylpiperazine (5.81 mL, 52.5 mmol), HOBT (7 g, 52.5 mmol) and EDC (10.2 g, 52.5 mmol) were added thereto, in turn. The reaction solution was stirred for 12 hours at room temperature and concentrated in vacuo. The residue was diluted with EtOAc and washed with saturated NaHCO$_3$ aqueous solution, water and 1N HCl. The extracted organic solution was dried over MgSO$_4$ and concentrated in vacuo. The residue was purified by column chromatography (eluent: MC/MeOH=10/1) to give the title compound (11.67 g, 93%).

MS[M+H]=339 (M+1)

Step C: (2S,4S)-1-Boc-4-amino-2-[(4-methylpiperazin-1-yl)carbonyl]pyrrolidine (2S,4S)-1-Boc-4-azido-2-[(4-methylpiperazin-1-yl)carbonyl]pyrrolidine (11.67 g, 34.48 mmol) obtained in Step B was dissolved in THF (30 mL). Trimethyl phosphine (3.40 mL, 38.37 mmol) was added dropwise thereto at 0~5° C. The reaction solution was stirred for 2 hours at room temperature, concentrated in vacuo and basified with saturated NaHCO$_3$ aqueous solution. The solution was extracted with EtOAc two times and concentrated in vacuo to give the title compound in oil form (10.61 g, 98.5%).

MS[M+H]=313 (M+1)

Step D: (2S,4S)-1-Boc-4-[(2,4-difluorophenyl)amino]-2-[(4-methylpiperazin-1-yl)carbonyl]pyrrolidine (2S,4S)-1-Boc-4-amino-2-[(4-methylpiperazin-1-yl)carbonyl]pyrrolidine (10.61 g, 33.96 mmol) obtained in Step C was dissolved in toluene (100 mL). Sodium t-butoxide (3.73 g, 38.81 mmol), 2-(di-t-butylphosphino)biphenyl (863 mg, 2.89 mmol), Tris(dibenzylideneacetone)-dipalladium(0) (1.73 g, 1.93 mmol) and 1-bromo-2,4-difluorobenzene (7.48 g, 38.81 mmol) were added thereto and the reaction solution was stirred for 10 hours at 110° C. After the reaction was completed, solid like material was filtered using the Cellite from the reaction solution. The reaction solution was diluted with EtOAc and washed with water. The extracted organic solution was dried over MgSO$_4$, concentrated in vacuo and purified by column chromatography (eluent: MC:MeOH=10/1) to give the title compound (11.24 g, 78%).

MS[M+H]=425 (M+1)

Step E: (2S,4S)-1-Boc-4-{(2,4-difluorophenyl)[(2S)-tetrahydrofuran-2-ylcarbonyl]amino}-2-[(4-methylpiperazin-1-yl)carbonyl]pyrrolidine (2S,4S)-1-Boc-4-[(2,4-difluorophenyl)amino]-2-[(4-methylpiperazin-1-yl)carbonyl]pyrrolidine (11.24 g, 26.48 mmol) obtained in Step D was reacted according to the same procedure as in the Step A of Example 3 to give the title compound (11.76 g, 85%).

MS[M+H]=523 (M+1)

Step F: (2S)—N-(2,4-difluorophenyl)-N-{(3S,5S)-5-[(4-methylpiperazin-1-yl)carbonyl]pyrrolidin-3-yl}tetrahydrofuran-2-carboxamide (2S,4S)-1-Boc-4-{(2,4-difluorophenyl)[2S]-tetrahydrofuran-2-ylcarbonyl]amino}-2-[(4-methylpiperazin-1-yl)carbonyl]pyrrolidine (11.76 g, 22.50 mmol) obtained in Step E was reacted according to the same procedure as in the Step E of Example 1 to give the title compound (9.49 g, 99.8%).

MS[M+H]=423 (M+1)

Step G: (2S)—N-{[(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl]-N-(2,4-difluorophenyl)tetrahydrofuran-2-carboxamide TFA salt (2S)—N-(2,4-difluorophenyl)-N-{(3S,5S)-5-[(4-methylpiperazin-1-yl)carbonyl]pyrrolidin-3-yl}tetrahydrofuran-2-carboxamide (9.49 g, 22.46 mmol) obtained in Step F was reacted according to the same procedure as in the Step F of Example 1 to give the title compound (13.10 g, 85%).

MS[M+H]=686 (M+1)

$^1$H NMR (500 MHz, DMSO-d$_6$, 140° C.) δ 7.41-7.28 (m, 5H), 7.27-7.21 (m, 1H), 7.13-7.07 (m, 1H), 4.79-4.71 (br, 1H), 4.57-4.45 (br, 1H), 4.06-4.00 (m, 1H), 3.82-3.67 (m, 5H), 3.67-3.50 (m, 7H), 3.39-3.17 (m, 3H), 2.91-2.72 (m, 3H), 2.59 (s, 3H), 1.96-1.89 (m, 1H), 1.89-1.80 (m, 1H), 1.80-1.66 (m, 2H), 1.59-1.47 (m, 1H), 1.37 (s, 9H), 1.35-1.23 (m, 1H)

Examples 78~84

Compounds of Preparations 1-23 were reacted according to the same procedure as
Example 77 to give compounds of following Examples.

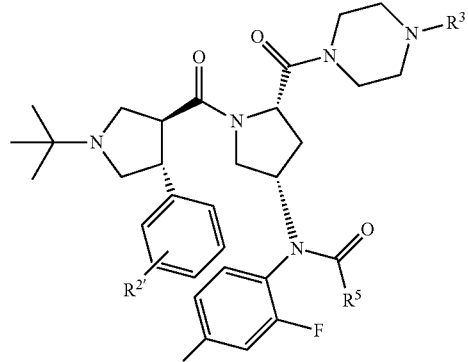

| Example | R$^{2'}$ | R$^3$ | R$^5$ | MS (M + 1) |
|---|---|---|---|---|
| 78 | 4-Cl | H | i-Pr | 644 |
| 79 | 4-Cl | Me | i-Pr | 658 |
| 80 | 4-Cl | Me | t-Bu | 672 |
| 81 | 4-Cl | H | t-Bu | 658 |
| 82 | 2,4-diF | Me | t-Bu | 674 |

-continued

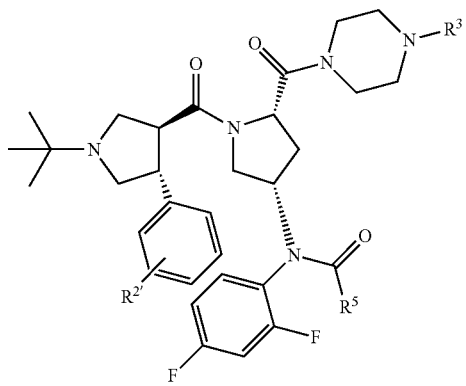

| Example | R²' | R³ | R⁵ | MS (M + 1) |
|---|---|---|---|---|
| 83 | 4-Cl | Me | furan | 682 |
| 84 | 2,4-diF | Me | furan | 684 |

Example 82

TFA Salt $^1$H NMR (500 MHz, DMSO-$d_6$, 140° C.) δ 7.63-7.50 (m, 1H), 7.41-7.32 (m, 1H), 7.28-7.18 (m, 1H), 7.15-6.98 (m, 3H), 4.77-4.66 (br, 1H), 4.54-4.40 (br, 1H), 4.01-3.89 (m, 1H), 3.82-3.53 (m, 8H), 3.40-3.26 (m, 2H), 3.17-2.97 (m, 4H), 2.74 (s, 3H), 2.48-2.32 (m, 1H), 1.53-1.21 (m, 2H), 1.37 (s, 9H), 0.95 (s, 9H)

Example 83

TFA Salt $^1$H NMR (500 MHz, DMSO-$d_6$, 140° C.) δ 7.48-7.44 (m, 1H), 7.43-7.30 (m, 5H), 7.26-7.18 (m, 1H), 7.13-7.05 (m, 1H), 6.38-6.34 (m, 1H), 6.30-6.25 (m, 1H), 4.86-4.75 (br, 1H), 4.71-4.59 (br, 1H), 3.88-3.50 (m, 8H), 3.41-3.20 (m, 3H), 3.11-2.92 (m, 4H), 2.71 (s, 3H), 2.62-2.46 (m, 1H), 1.73-1.63 (m, 1H), 1.44-1.32 (m, 1H), 1.38 (s, 9H)

Physiological activity of the compounds of the present invention was assessed by measuring agonistic activity as well as binding activity for melanocortin receptors (MCR) according to methods A and B explained as follows.

A. Luciferase Assay

As one of the methods to measure MCR agonistic activity of the compound according to the present invention, the expression level of a marker gene (for example, luciferase) which increases proportionally according to the increase of cAMP content in the cell, was measured.

First, permanent expression HEK (Human Embryonic Kidney) cell lines (HEK MC1R-Luc, MC3R-Luc, MC4R-Luc or MC5R-Luc) expressing the MCR gene of each sub-type together with luciferase gene (CRE-LUC) under the control of CRE (cAMP Response Element) were constructed. The above cell lines were incubated in an incubator with 6% $CO_2$ atmosphere at 37° C. using selection medium, DMEM (Dulbecco's Modified Eagles Medium) containing 10% heat-inactivated fetal bovine serum (Gibco/BRL), 100 unit/ml, penicillin (Gibco/BRL), 100 unit/ml streptomycin (Gibco/BRL), and 200 μg/ml geneticin (G418) (Gibco/BRL). When the cell covered 70% of total surface of the culture dish with 100 mm diameter, the culture dish was rinsed one time with 10 ml Phosphate Buffered Saline (PBS) free of $Ca^{++}$ and $Mg^{++}$, and then 3 ml PBS solution containing 0.05% trypsin and 0.53 mM EDTA was added thereto. After the trypsin/EDTA solution was removed, the cell lines were incubated in a thermostatic incubator for 1 minute at 37° C., and resuspended in 10 ml selection medium and centrifuged for 5 minutes at 1500 rpm. The supernatant was discarded and the settled cells were resuspended in 5 ml selection medium free of Phenol Red. The resulting cell-suspension was plated onto each well of 96-well culture plates for Luminometer (Costar) with a concentration of 5×10⁴ cell in 100 μl culture medium for each well and incubated in the incubator with 6% CO2 atmosphere at 37° C. for 18 hours. With MCR agonists (Example compounds) diluted stepwise using the above culture medium, the cells were treated under the condition of the final DMSO concentration not exceeding 1%, and incubated for 5 hours in the atmosphere of 6% $CO_2$ at 37° C. Then, 50 μl Bright-Glo (Promega) was added to each well. After allowing the treated cells to be at room temperature for 15 minutes, luminescence was measured for each well by using luminometer (Victor). The level of luminescence induced by the stepwise-diluted agonist was converted to relative % value to those by the treatment of 10 μM NDP-MSH. The $EC_{50}$ indicates the concentration of each agonist for inducing 50% of maximal luminescence by each agonist and this value was measured by a statistical software (Prizm).

B. cAMP Accumulation Assay

As another method to measure MCR agonistic activity of the compound according to the present invention, an increase of cAMP amount in the cell was measured.

First, permanent expression HEK (Human Embryonic Kidney) cell lines (HEK MC1R-Luc, MC3R-Luc, MC4R-Luc or MC5R-Luc) expressing the MCR gene of each sub-type were plated onto each well of 24-well culture plates for Luminometer (Costar) with a concentration of 2×10⁵ cell in 1 ml culture medium for each well, and then incubated in an incubator with 6% $CO_2$ atmosphere at 37° C. for 24 hours. The medium was removed from each well followed by rinsing with 0.5 ml cold DMEM one time. With MCR agonists (Example compounds) diluted stepwise using 200 μl DMEM including 500 μM IBMX (isobutylmethylxanthine), the cells were treated under the condition of the final DMSO concentration not exceeding 1%, and incubated for 30 minutes in the atmosphere of 6% $CO_2$ at 37° C. Then, the cAMP amount in each cell was measured using Amersham cAMP assay Kit (TRK432).

More specifically, 14.4 μl of 6M PCA (60%) was added to each well, and allowed to be in ice for 10 minutes, and 200 μl sample was taken from each well and transferred to microcentrifuge tube. 11 μl of 5M KOH/1M Tris was added thereto for neutralization and centrifuged at 12,000 rpm for 1 minute. 50 μl of supernatant was taken and 500 of $^3$H labeled cAMP (0.9 pmol, 0.025 μCi) and 100 μl binding protein was added thereto, and shaken for 5 seconds. After allowing the treated sample to be in ice for 2 hours, 100 μl charcoal was added thereto and centrifuged for 3 minutes at 4° C. under 12,000 rpm. 200 μl of supernatant was taken and transferred to scintillation vial. 5 ml scintillant was added to the vial and radioactivity was measured. The amount of c-AMP induced by the stepwise-diluted agonist was converted to relative % value to those by the treatment of 10 μM NDP-MSH. $EC_{50}$ indicates the concentration of each agonist for inducing 50% of maximal c-AMP amount by each agonist and this value was measured by a statistical software (Prizm).

As a result of measurement according to the above explained methods, the example compounds according to the present invention showed agonistic activity to each MCR. In particular, the compounds according to the present invention showed excellent agonistic activity to MC4R with the $EC_{50}$ values from 0.0001 μM to 0.1 μM. Specifically, the compounds of Examples 1, 2, 3, 4, 8, 9, 10, 11, 12, 13, 14, 15, 16, 17, 18, 19, 20, 21, 22, 23, 24, 26, 30, 32, 34, 35, 36, 37, 38, 39, 41, 43, 45, 49, 50, 52, 53, 54, 58, 59, 60, 65, 66, 68, 69, 72, 73, 78, 80, 81 and 82 of the present invention showed an $EC_{50}$ value in the range of 0.1~10 nM; those of Examples 5, 6, 7, 31, 33, 42, 44, 46, 47, 48, 51, 55, 56, 57, 62, 63, 64, 74, 77, 79 and 83 showed an $EC_{50}$ value in the range of 10~100 nM; those of Examples 27, 28, 29, 70, 76 and 84 showed an $EC_{50}$ value in the range of 100~1000 nM; and those of Examples 67, 71 and 75 showed an $EC_{50}$ value in the range of 1000~10000 nM.

For example, the specific activities of representative compounds are represented in the following table:

| Examples | $EC_{50}$ (nM) |
|---|---|
| 1 | 10 |
| 2 | 6 |
| 3 | 3 |
| 4 | 0.2 |
| 16 | 0.4 |
| 26 | 6 |
| 32 | 4 |
| 41 | 3 |
| 43 | 10 |
| 45 | 8 |

The invention claimed is:

1. A compound of the following formula 1,

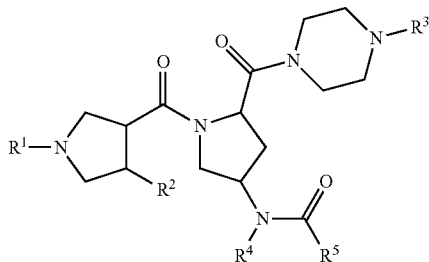

(1)

wherein
$R^1$ represents hydrogen, or represents $C_1$-$C_{10}$-alkyl, $C_3$-$C_7$-cycloalkyl, $C_6$-$C_{10}$-aryl, heterocycle or heteroaryl, each of which is unsubstituted or substituted with at least one substituent selected from the group consisting of halogen, amino, $C_1$-$C_4$-alkyl, trifluoromethyl, hydroxy, $C_1$-$C_4$-alkoxy, cyano and oxo;
$R^2$ represents phenyl or six-membered heteroaryl, each of which is unsubstituted or mono- or di-substituted with substituent(s) selected from the group consisting of halogen, hydroxy, $C_1$-$C_4$-alkyl, $C_1$-$C_4$-alkoxy, cyano and amino;
$R^3$ represents hydrogen, or represents $C_1$-$C_6$-alkyl or $C_3$-$C_7$-cycloalkyl, each of which is unsubstituted or substituted with substituent(s) selected from the group consisting of halogen, methyl, trifluoromethyl, hydroxy and amino;
$R^4$ represents $C_4$-$C_7$-cycloalkyl or monocyclic heterocycle, each of which is unsubstituted or mono- or poly-substituted with substituent(s) selected from the group consisting of halogen, hydroxy, $C_1$-$C_4$-alkyl, trifluoromethyl, $C_1$-$C_4$-alkoxy and oxo; or represents phenyl or six-membered heteroaryl, each of which is unsubstituted or mono- or di-substituted with substituent(s) selected from the group consisting of halogen, hydroxy, $C_1$-$C_4$-alkyl, trifluoromethyl, $C_1$-$C_4$-alkoxy and amino; and
$R^5$ represents $C_1$-$C_6$-alkyl, difluoromethyl, trifluoromethyl, $C_3$-$C_8$-cycloalkyl, amino, $C_1$-$C_4$-alkylamino, di($C_1$-$C_4$-alkyl)amino, phenyl, monocyclic heteroaryl or monocyclic heterocycle where alkyl is unsubstituted or substituted with at least one substituent selected from the group consisting of fluoro, hydroxy, mercapto, $C_1$-$C_4$ alkoxy, acetoxy, amino, acetylamino, cyano, carbamoyl, dimethyl carbamoyl and oxo and phenyl or heteroaryl is unsubstituted or mono- or di-substituted with substituent(s) selected from the group consisting of halogen, hydroxy, methyl, trifluoromethyl, methoxy and amino, in which, heteroaryl represents imidazole, oxazole, thiazole, pyrazole, triazole, pyridine, pyrimidine, pyridazine or furan, and heterocycle represents oxazoline, imidazoline, thiazoline, tetrahydropyran, tetrahydrothiopyran, piperidine, tetrahydrofuran or dihydrofuran,
or pharmaceutically acceptable salt or stereoisomer thereof.

2. The compound of formula 1 according to claim 1, wherein $R^1$ represents hydrogen, methyl, ethyl, trifluoroethyl, propyl, isopropyl, butyl, isobutyl, tert-butyl, cyclopropyl, cyclobutyl, cyclopentyl or cyclohexyl; or represents phenyl, oxazolinyl, imidazolinyl, thiazolinyl, tetrahydropyranyl, tetrahydrothiopyranyl, imidazolyl, oxazolyl, thiazolyl, pyrazolyl, triazolyl, pyridinyl, pyrimidinyl, piperidinyl or pyridazinyl, each of which is unsubstituted or substituted with substituent(s) selected from the group consisting of halogen, methyl, cyano, oxo and hydroxy,
or pharmaceutically acceptable salt or stereoisomer thereof.

3. The compound of formula 1 according to claim 2, wherein $R^1$ represents isopropyl, tert-butyl or cyclopropyl; or represents phenyl, tetrahydropyranyl, thiazolyl, pyridinyl, pyrimidinyl or pyridazinyl, each of which is unsubstituted or substituted with substituent(s) selected from the group consisting of halogen, methyl, cyano and hydroxy,
or pharmaceutically acceptable salt or stereoisomer thereof.

4. The compound of formula 1 according to claim 1, wherein $R^2$ represents phenyl which is unsubstituted or mono- or di-substituted with substituent(s) selected from the group consisting of fluorine, chlorine, bromine, methoxy and methyl,
or pharmaceutically acceptable salt or stereoisomer thereof.

5. The compound of formula 1 according to claim 4, wherein $R^2$ represents 4-chlorophenyl or 2,4-difluorophenyl,
or pharmaceutically acceptable salt or stereoisomer thereof.

6. The compound of formula 1 according to claim 1, wherein $R^3$ represents hydrogen, methyl, ethyl, propyl, isopropyl, butyl, isobutyl, tert-butyl, cyclopropyl, cyclobutyl or cyclopentyl, or pharmaceutically acceptable salt or stereoisomer thereof.

7. The compound of formula 1 according to claim 6, wherein $R^3$ represents hydrogen, methyl, ethyl or isopropyl,
or pharmaceutically acceptable salt or stereoisomer thereof.

8. The compound of formula 1 according to claim 1, wherein $R^4$ represents cyclopentyl, cyclohexyl, cycloheptyl, 4-methylcyclohexyl, 4,4-dimethylcyclohexyl, 4-fluorocyclohexyl, 4,4-difluorocyclohexyl or 4-trifluoromethyl-cyclohexyl; or represents phenyl which is unsubstituted or mono- or di-substituted with substituent(s) selected from the group consisting of fluorine, chlorine, methyl and methoxy,
or pharmaceutically acceptable salt or stereoisomer thereof.

9. The compound of formula 1 according to claim 8, wherein $R^4$ represents cyclohexyl, 4-methylcyclohexyl, 4,4-dimethylcyclohexyl, 4,4-difluorocyclohexyl or 2,4-difluorophenyl,
or pharmaceutically acceptable salt or stereoisomer thereof.

10. The compound of formula 1 according to claim 1, wherein $R^5$ represents methyl, trifluoromethyl, hydroxymethyl, methoxymethyl, ethoxymethyl, propyl, isopropyl, isobutyl, tert-butyl, —$CH_2CH_2OH$, —$CH(CH_3)CH_2OH$, —$C(CH_3)_2CH_2OH$, —$C(CH_3)(CH_2OH)_2$, —$C(CH_3)_2CH_2OMe$, —$C(CH_3)_2CH_2OEt$, phenyl, oxazolinyl, imidazolinyl, thiazolinyl, tetrahydropyranyl, imidazolyl, oxazolyl, thiazolyl, pyrazolyl, triazolyl, furanyl, tetrahydrofuranyl, dihydrofuranyl, tetrahydropyranyl, pyridinyl or piperidinyl,
or pharmaceutically acceptable salt or stereoisomer thereof.

11. The compound of formula 1 according to claim 10, wherein $R^5$ represents isopropyl, tert-butyl, —$C(CH_3)_2CH_2OH$, furanyl or tetrahydrofuranyl,
or pharmaceutically acceptable salt or stereoisomer thereof.

12. The compound of formula 1 according to claim 1, wherein
$R^1$ represents isopropyl, tert-butyl or cyclopropyl; or represents phenyl, tetrahydropyranyl, thiazolyl, pyridinyl, pyrimidinyl or pyridazinyl, each of which is unsubstituted or substituted with substituent(s) selected from the group consisting of halogen, methyl, cyano and hydroxy;
$R^2$ represents 4-chlorophenyl or 2,4-difluorophenyl;
$R^3$ represents hydrogen, methyl, ethyl or isopropyl;
$R^4$ represents cyclohexyl, 4-methylcyclohexyl, 4,4-dimethylcyclohexyl, 4,4-difluorocyclohexyl or 2,4-difluorophenyl; and
$R^5$ represents isopropyl, tert-butyl, —$C(CH_3)_2CH_2OH$, furanyl or tetrahydrofuranyl,
or pharmaceutically acceptable salt or stereoisomer thereof.

13. The compound of formula 1 according to claim 12 which is selected from the group consisting of the following:
N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)acetamide;
N-[(3S,5S)-1-{[(3S,4R)-1-tert-butyl-4-(2,4-difluorophenyl)pyrrolidin-3-yl]carbonyl}-5-(piperazin-1-ylcarbonyl)pyrrolidin-3-yl]-N-(4,4-dimethylcyclohexyl)acetamide;
(2S)—N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;
N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)-3-hydroxy-2,2-dimethylpropanamide;
N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)acetamide;
N-{(3S,5S)-1-{[(3S,4R)-1-tert-butyl-4-(2,4-difluorophenyl)pyrrolidin-3-yl]carbonyl}-5-[(4-ethylpiperazin-1-yl)carbonyl]pyrrolidin-3-yl}-N-(4,4-dimethylcyclohexyl)acetamide;
N-{(3S,5S)-1-{[(3S,4R)-1-tert-butyl-4-(2,4-difluorophenyl)pyrrolidin-3-yl]carbonyl}-5-[(4-isopropylpiperazin-1-yl)carbonyl]pyrrolidin-3-yl}-N-(4,4-dimethylcyclohexyl)acetamide;
N-{(3S,5S)-1-{[(3S,4R)-1-tert-butyl-4-(4-chlorophenyl)pyrrolidin-3-yl]carbonyl}-5-[(4-ethylpiperazin-1-yl)carbonyl]pyrrolidin-3-yl}-N-(4,4-dimethylcyclohexyl)acetamide;
N-{(3S,5S)-1-{[(3S,4R)-1-tert-butyl-4-(4-chlorophenyl)pyrrolidin-3-yl]carbonyl}-5-[(4-isopropylpiperazin-1-yl)carbonyl]pyrrolidin-3-yl}-N-(4,4-dimethylcyclohexyl)acetamide;
N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;
N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;
(2S)—N-{(3S,5S)-1-{[(3S,4R)-1-tert-butyl-4-(4-chlorophenyl)pyrrolidin-3-yl]carbonyl}-5-[(4-ethylpiperazin-1-yl)carbonyl]pyrrolidin-3-yl}-N-(4,4-dimethylcyclohexyl)tetrahydrofuran-2-carboxamide;
(2S)—N-{(3S,5S)-1-{[(3S,4R)-1-tert-butyl-4-(4-chlorophenyl)pyrrolidin-3-yl]carbonyl}-5-[(4-isopropylpiperazin-1-yl)carbonyl]pyrrolidin-3-yl}-N-(4,4-dimethylcyclohexyl)tetrahydrofuran-2-carboxamide;
(2S)—N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;
N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)-3-hydroxy-2,2-dimethylpropanamide;
(2S)—N-{(3S,5S)-1-{[(3S,4R)-1-tert-butyl-4-(4-chlorophenyl)pyrrolidin-3-yl]carbonyl-5-[(4-methylpiperazin-1-yl)carbonyl]pyrrolidin-3-yl}-N-(cis-4-methylcyclohexyl)tetrahydrofuran-2-carboxamide;
N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-2,2-dimethyl-N-(cis-4-methylcyclohexyl)propanamide;
N-{(3S,5S)-1-[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-2,2-dimethyl-N-(cis-4-methylcyclohexyl)propanamide;
N-{(3S,5S)-1-[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-3-hydroxy-2,2-dimethyl-N-(cis-4-methylcyclohexyl)propanamide;

N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-3-hydroxy-2,2-dimethyl-N-(cis-4-methylcyclohexyl)propanamide;

(2S)—N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-1-tert-butyl-4-(4-chlorophenyl)pyrrolidin-3-yl]carbonyl}-5-[(4-ethylpiperazin-1-yl)carbonyl]pyrrolidin-3-yl}-N-(cis-4-methylcyclohexyl)tetrahydrofuran-2-carboxamide;

(2S)—N-{(3S,5S)-1-[(3S,4R)-1-tert-butyl-4-(4-chlorophenyl)pyrrolidin-3-yl]carbonyl}-5-[(4-isopropylpiperazin-1-yl)carbonyl]pyrrolidin-3-yl}-N-(cis-4-methylcyclohexyl)tetrahydrofuran-2-carboxamide;

N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(cis-4-methylcyclohexyl)-3-furamide;

(2R)—N-{(3S,5S)-1-{[(3S,4R)-1-tert-butyl-4-(4-chlorophenyl)pyrrolidin-3-yl]carbonyl-5-[(4-methylpiperazin-1-yl)carbonyl]pyrrolidin-3-yl}-N-(cis-4-methylcyclohexyl)tetrahydrofuran-2-carboxamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-difluorocyclohexyl)-2,2-dimethylpropanamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-difluorocyclohexyl)acetamide;

N-{(3S,5S)-1-{[(3S,4R)-1-tert-butyl-4-(4-chlorophenyl)pyrrolidin-3-yl]carbonyl}-5-[(4-ethylpiperazin-1-yl)carbonyl]pyrrolidin-3-yl}-N-(4,4-difluorocyclohexyl)acetamide;

N-{(3S,5S)-1-[(3S,4R)-1-tert-butyl-4-(4-chlorophenyl)pyrrolidin-3-yl]carbonyl}-5-[(4-isopropylpiperazin-1-yl)carbonyl]pyrrolidin-3-yl}-N-(4,4-difluorocyclohexyl)acetamide;

N-{(3S,5S)-1-[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-difluorocyclohexyl)-2,2-dimethylpropanamide;

(2S)—N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-difluorocyclohexyl)tetrahydrofuran-2-carboxamide;

(2S)—N-{(3S,5R)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

N-{(3S,5R)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-2,2-dimethyl-N-(cis-4-methylcyclohexyl)propanamide;

(2S)—N-{(3S,5R)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5R)-1-[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

N-{(3S,5R)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-3-hydroxy-2,2-dimethyl-N-(cis-4-methylcyclohexyl)propanamide;

N-{(3S,5R)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)acetamide;

N-{(3S,5R)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(cis-4-methylcyclohexyl)acetamide;

N-{(3S,5R)-1-{[(3S,4R)-1-tert-butyl-4-(4-chlorophenyl)pyrrolidin-3-yl]carbonyl}-5-[(4-isopropylpiperazin-1-yl)carbonyl]pyrrolidin-3-yl}-N-(cis-4-methylcyclohexyl)acetamide;

(2R)—N-{(3S,5R)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(4-chlorophenyl)-1-(6-methylpyridazine-3-yl)pyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(2,4-difluorophenyl)-1-(6-chloropyridazine-3-yl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-4-(2,4-difluorophenyl)-1,6-dihydropyridazine-3-ylpyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(4-chlorophenyl)-1-phenylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-4-(2,4-difluorophenyl)-1-(tetrahydro-2H-pyran-4-yl)pyrrolidin-3-yl]carbonyl}-5-[(4-isopropylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(2,4-difluorophenyl)-1-(tetrahydro-2H-thiopyran-4-yl)pyrrolidin-3-yl]carbonyl}-5-[(4-isopropylpiperazin-1-yl)carbonyl]pyrrolidin-3-yl}-N-(4,4-dimethylcyclohexyl)tetrahydrofuran-2-carboxamide;

N-{(3S,5S)-1-{[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4,4-dimethylcyclohexyl)-3-hydroxy-2,2-dimethylpropanamide;

N-{(3S,5S)-1-{[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4,4-difluorocyclohexyl)-2,2-dimethylpropanamide;

(2S)—N-{(3S,5S)-1-{[(3S,4R)-4-(4-chlorophenyl)-1-(tetrahydro-2H-pyran-4-yl)pyrrolidin-3-yl]carbonyl}-

5-[(4-methylpiperazin-1-yl)carbonyl]pyrrolidin-3-yl}-N-(4,4-difluorocyclohexyl)tetrahydrofuran-2-carboxamide;

(2S)—N-{(3S,5R)-1-{[(3S,4R)-4-(2,4-difluorophenyl)-1-(tetrahydro-2H-pyran-4-yl)pyrrolidin-3-yl]carbonyl}-5-[(4-isopropylpiperazin-1-yl)carbonyl]pyrrolidin-3-yl}-N-(4,4-dimethylcyclohexyl)tetrahydrofuran-2-carboxamide;

N-{(3S,5S)-1-{[(3S,4R)-4-(2,4-difluorophenyl)-1-(tetrahydro-2H-pyran-4-yl)pyrrolidin-3-yl]carbonyl}-5-[(4-methylpiperazin-1-yl)carbonyl]pyrrolidin-3-yl}-2,2-dimethyl-N-(cis-4-methylcyclohexyl)propanamide;

N-{(3S,5R)-1-{[(3S,4R)-4-(4-chlorophenyl)-1-(tetrahydro-2H-pyran-4-yl)pyrrolidin-3-yl]carbonyl}-5-[(4-methylpiperazin-1-yl)carbonyl]pyrrolidin-3-yl}-N-(4-methylcyclohexyl)acetamide;

(2S)—N-{(3S,5R)-1-{[(3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5R)-1-{[(3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

N-{(3S,5S)-1-{[(3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(4,4-dimethylcyclohexyl)-3-hydroxy-2,2-dimethylpropanamide;

N-{(3S,5S)-1-{[(3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(cis-4-methylcyclohexyl)-3-hydroxy-2,2-dimethylpropanamide;

N-{(3S,5S)-1-{[(3S,4R)-1-cyclopropyl-4-(2,4-difluorophenyl)pyrrolidin-3-yl]carbonyl}-5-[(4-methylpiperazin-1-yl)carbonyl]pyrrolidin-3-yl}-N-(cis-4-methylcyclohexyl)-3-hydroxy-2,2-dimethylpropanamide;

N-{(3S,5S)-1-{[(3S,4R)-4-(4-chlorophenyl)-1-cyclopropylpyrrolidin-3-yl]carbonyl}-5-[(4-methylpiperazin-1-yl)carbonyl]pyrrolidin-3-yl}-N-(4,4-difluorocyclohexyl)-3-hydroxy-2,2-dimethylpropanamide;

N-{(3S,5R)-1-{[(3S,4R)-4-(4-chlorophenyl)-1-isopropylpyrrolidin-3-yl]carbonyl}-5-[(4-methylpiperazin-1-yl)carbonyl]pyrrolidin-3-yl}-N-(cis-4-methylcyclohexyl)acetamide;

N-{(3S,5S)-1-{[(3S,4R)-4-(4-chlorophenyl)-1-(6-methylpyridazine-3-yl)pyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;

N-{(3S,5S)-1-{[(3S,4R)-4-(4-chlorophenyl)-1-pyridine-2-ylpyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;

(2S)—N-{(3S,5S)-1-{[(3S,4R)-4-(4-chlorophenyl)-1-pyridine-2-ylpyrrolidin-3-yl]carbonyl}-5-[(4-methylpiperazin-1-yl)carbonyl]pyrrolidin-3-yl}-N-(4,4-dimethylcyclohexyl)tetrahydrofuran-2-carboxamide;

(2S)—N-{(3S,5S)-1-{[(3S,4R)-4-(2,4-difluorophenyl)-1,6-dihydropyridazine-3-ylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

N-{(3S,5S)-1-{[(3S,4R)-4-(4-chlorophenyl)-1-pyrimidine-2-ylpyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;

(2S)—N-{(3S,5S)-1-{[(3S,4R)-4-(2,4-difluorophenyl)-1-pyridine-2-ylpyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-4-(4-chlorophenyl)-1-(5-cyanopyridine-2-yl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

N-{(3S,5S)-1-{[(3S,4R)-4-(4-chlorophenyl)-1-(1,3-thiazole-2-yl)pyrrolidin-3-yl]carbonyl}-5-[(4-methylpiperazin-1-yl)carbonyl]pyrrolidin-3-yl}-N-(4,4-dimethylcyclohexyl)-2,2-dimethylpropanamide;

(2S)—N-{(3S,5S)-1-{[(3S,4R)-4-(4-chlorophenyl)-1-(2-methylphenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-4-(4-chlorophenyl)-1-(1-methyl-6-oxo-1,6-dihydropyridazine-3-yl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-4-(4-chlorophenyl)-1-(6-oxo-1,6-dihydropyridazine-3-yl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3R,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4S)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3R,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(cis-4-methylcyclohexyl)tetrahydrofuran-2-carboxamide;

(2S)—N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(2,4-difluorophenyl)tetrahydrofuran-2-carboxamide;

N-[(3S,5S)-1-{[(3S,4R)-1-tert-butyl-4-(4-chlorophenyl)pyrrolidin-3-yl]carbonyl}-5-(piperazin-1-yl carbonyl)pyrrolidin-3-yl]-N-(2,4-difluorophenyl)-2-methylpropanamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(2,4-difluorophenyl)-2-methylpropanamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(2,4-difluorophenyl)-2,2-dimethylpropanamide;

N-[(3S,5S)-1-{[(3S,4R)-1-tert-butyl-4-(4-chlorophenyl)pyrrolidin-3-yl]carbonyl}-5-(piperazin-1-ylcarbonyl)pyrrolidin-3-yl]-N-(2,4-difluorophenyl)-2,2-dimethylpropanamide;

N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(2,4-difluorophenyl)-2,2-dimethylpropanamide;

N-{(3S,5S)-1-{[(3S,4R)-1-tert-butyl-4-(4-chlorophenyl)pyrrolidin-3-yl]carbonyl}-5-[(4-methylpiperazin-1-yl)carbonyl]pyrrolidin-3-yl}-N-(2,4-difluorophenyl)-2-furamide; and N-{(3S,5S)-1-{[(3S,4R)-1-tert-butyl-4-(2,4-difluorophenyl)pyrrolidin-3-yl]carbonyl}-5-[(4-methylpiperazin-1-yl)carbonyl]pyrrolidin-3-yl}-N-(2,4-difluorophenyl)-2-furamide, or pharmaceutically acceptable salt or stereoisomer.

14. An agonistic composition to melanocortin receptor comprising the compound of formula 1 as defined in claim 1, or pharmaceutically acceptable salt or stereoisomer thereof as an active ingredient, together with pharmaceutically acceptable carrier.

15. A method for treatment of obesity comprising administering the composition according to claim 14 to a subject in need thereof.

* * * * *